United States Patent [19]
Yin et al.

[11] Patent Number: 5,631,329
[45] Date of Patent: May 20, 1997

[54] PROCESS FOR PRODUCING HYPER-COMB-BRANCHED POLYMERS

[75] Inventors: Rui Yin, Mount Pleasant; Donald A. Tomalia, Midland; David M. Hedstrand, Midland; Douglas R. Swanson, Midland, all of Mich.

[73] Assignee: Dendritech, Inc., Midland, Mich.

[21] Appl. No.: 408,833

[22] Filed: Mar. 21, 1995

Related U.S. Application Data

[63] Continuation-in-part of Ser. No. 376,100, Jan. 20, 1995, which is a continuation-in-part of Ser. No. 4,849, Jan. 19, 1993, abandoned, which is a continuation-in-part of Ser. No. 739,167, Aug. 1, 1991, abandoned, which is a continuation-in-part of Ser. No. 573,362, Aug. 27, 1990, abandoned.

[51] Int. Cl.⁶ .................................................. C08F 293/00
[52] U.S. Cl. .................... 525/417; 525/902; 525/91; 525/279; 525/280; 525/326.8
[58] Field of Search ............................... 525/417, 902, 525/91, 279, 280, 326.8

[56] References Cited

U.S. PATENT DOCUMENTS

| | | | |
|---|---|---|---|
| 4,435,548 | 3/1984 | Tomalia et al. | 525/451 |
| 4,507,466 | 3/1985 | Tomalia et al. | 528/332 |
| 4,544,724 | 10/1985 | Sogah et al. | 526/279 |
| 4,558,120 | 12/1985 | Tomalia et al. | 528/363 |
| 4,568,737 | 2/1986 | Tomalia et al. | 528/332 |
| 4,587,329 | 5/1986 | Tomalia et al. | 528/363 |
| 4,599,400 | 7/1986 | Tomalia et al. | 528/405 |
| 4,631,337 | 12/1986 | Tomalia et al. | 528/391 |
| 4,694,064 | 9/1987 | Tomalia et al. | 528/332 |
| 4,713,975 | 12/1987 | Tomalia et al. | 73/865.8 |
| 4,737,550 | 4/1988 | Tomalia et al. | 525/418 |
| 4,758,635 | 7/1988 | Wilson et al. | 525/418 |
| 4,847,328 | 7/1989 | Hutchins et al. | 525/107 |
| 4,851,477 | 7/1989 | Hutchins et al. | 525/123 |
| 4,855,403 | 8/1989 | Meschke et al. | 528/419 |
| 4,857,218 | 8/1989 | Meschke et al. | 252/49.3 |
| 4,857,599 | 8/1989 | Tomalia et al. | 525/259 |
| 4,857,615 | 8/1989 | Bronn et al. | 526/173 |
| 4,857,618 | 8/1989 | Silver et al. | 526/240 |
| 4,871,779 | 10/1989 | Killat et al. | 521/28 |
| 4,906,691 | 3/1990 | Joseph et al. | 525/99 |
| 4,910,268 | 3/1990 | Kobayashi | 525/411 |
| 4,938,885 | 7/1990 | Migdal | 252/51.5 A |
| 4,946,824 | 8/1990 | Meschke et al. | 503/216 |
| 5,041,516 | 8/1991 | Frechet et al. | 528/44 |
| 5,124,246 | 6/1992 | Urdea et al. | 435/6 |
| 5,175,270 | 12/1992 | Nilsen et al. | 536/27 |

FOREIGN PATENT DOCUMENTS

| 9314147 | 7/1993 | WIPO . |
|---|---|---|

OTHER PUBLICATIONS

Nucleic Acids Research, vol. 17, No. 17, 1989, Thomas Horn et al., Forks and combs and DNA: the synthesis of branched oligodeoxy–ribonucleotides.
Compressed Air Magazine, Jun. 1992, pp. 12–17.
The Scientist, Research, Oct. 28, 1991, p. 16.
D.A. Tomalia, A.M. Naylor, W. A. Goddard, III, Angewandte Chemie, 29/2 (1990), pp. 138–175.
J. Polymer Sci., T. Altores et al., Part A, vol. 3, pp. 4131–4151 (1965).
Interscience Publishers, Preparative Methods of Polymer Chemistry, 2nd Ed., pp. 213–214 (1968).
American Chemical Society, "Comb–Burst Dendrimer Topology, New Macromolecular Architecture Derived From Dendritic Grafting," Feb. 5, 1991, pp. 1–4.

*Primary Examiner*—W. Robinson H. Clark
*Attorney, Agent, or Firm*—Price, Heneveld, Cooper, DeWitt & Litton

[57] ABSTRACT

The specification discloses a process for producing polybranched polymer having relatively high molecular weight by forming a first set of branches by polymerizing monomers which are either protected against or are non-reactive to branching and grafting during polymerization, grafting that first set of branches to a core having a plurality of reactive sites capable of reacting with the reactive end units of said branches, either deprotecting or activating a plurality of monomeric units on each of said branches to create branch reactive sites, forming a second set of branches in the same manner as the first set of branches were formed, grafting the second set of branches to the first set of branches by reacting the reactive end units of the second set of branches with each said branch reactive site on said first set of branches and repeating the foregoing steps reiteratively to form and attach subsequent sets of branches to prior branch sets until a desired number of iterations has been effected.

66 Claims, 3 Drawing Sheets

1

PROCESS FOR PRODUCING HYPER-COMB-BRANCHED POLYMERS

BACKGROUND OF THE INVENTION

This application is a continuation-in-part application of copending application Ser. No. 08/376,100, filed on Jan. 20 1995, which is a continuation in part application of Ser. No. 08/004,849, filed on Jan. 19, 1993, now abandoned, which is a continuation-in-part of application Ser. No. 07/739,167 filed Aug. 1, 1991, now abandoned, which is a continuation-in-part of application Ser. No. 07/573,362, filed Aug. 27, 1990, now abandoned.

This invention deals with non-crosslinked, poly-branched polymers having a comb-burst configuration and a process for preparing such polymers.

Macromolecular organic compounds having novel structures have been investigated for many years as academic curiosities and very little attention has been paid to their use in industrial applications. Since the early 1980's, there has been a renewed interest in the study and development of such macromolecular materials in order to control their critical molecular design parameters, for example, size, shape, surface chemistry, flexibility and topology, for use in industrial applications. These materials have found such diverse uses as demulsifiers for oil-in-water emulsions; as wet strength agents in the manufacture of paper, as agents for modifying viscosities in aqueous formulations such as paints and as submicron size calibrators. Certain biological uses have also been suggested for these materials.

Structurally, polymers are classified as either linear or branched wherein the term "branched" generally means that the individual molecular units of the branches are discrete from the polymer backbone, yet may have the same chemical constitution as the polymer backbone. Thus, regularly repeating side groups which are inherent in the monomeric structure and are of different chemical consitutution than the polymer backbone are not considered as "branches", that is, for example, the methyl groups pendent on a polydimethylsiloxane chain are not considered to be branches of that polymer.

in U.S. Pat. No. 4,507,466, issued Mar. 26, 1985, the patentees therein described the preparation of polymers having "branching" in the following manner:

"To produce a branched polymer, it is necessary to employ an initiator, a monomer, or both that possess at least three moieties that function in the polymerization reaction. Such monomer or initiators are often called polyfunctional. The simplest branched polymers are the chain branched polymers wherein a linear backbone bears one or more essentially linear pendant groups. This simple form of branching, often called comb branching, may be regular wherein the branches are uniformly and regularly distributed on the polymer backbone or irregular wherein the branches are distributed in non-uniform or random fashion on the polymer backbone." "An example of regular comb branching is a comb branched polystyrene as described by T. Altores et al. in J. Polymer Sci., Part A, Vol. 3 4131–4151 (1965) and an example of irregular comb branching is illustrated by graft copolymers as described by Sorenson et al. in "Preparative Methods of Polymer Chemistry", 2nd Ed., Interscience Publishers, 213–214 (1968).

Another type of branching is exemplified by crosslinked or network polymers wherein the polymer chains are connected via tetravalent compounds, e.g., polystyrene molecules bridged or cross-linked with divinylbenzene. In this type of branching, many of the individual branches are not linear, in that, each branch may itself contain groups pendant from a linear chain. More importantly in network branching, each polymer macromolecule (backbone) is cross-linked at two or more sites to other polymer macromolecules. Also the chemical constitution of the cross-linkages may vary from that of the polymer macromolecules. In this so-called cross-linked or network branched polymer, the various branches or cross-linkages may be structurally similar (called regular cross-linked) or they may be structurally dissimilar (called irregularly cross-linked). An example of regular cross-linked polymers is a ladder-type poly(phenylsilsesquinone) [sic.] {poly(phenylsilsesquioxane)}."

Sogah, et al., in the background of U.S. Pat. No. 4,544, 724, issued Oct. 1, 1985, discusses some of these types of polymers and gives a short review of the many publications and disclosures regarding them.

One of the inventors herein, Donald A. Tomalia, and many of his co-workers have been working in this field for several years and have issued many patents which disclose various non-crosslinked, macromolecular branched assemblies.

For example, U.S. Pat. No. 4,435,548, issued Mar. 6, 1984 discusses branched polyaraidoamines; U.S. Pat. No. 4,507, 466, issued Mar. 26, 1985, U.S. Pat. No. 4,558,120, issued Dec. 10, 1985, U.S. Pat. No. 4,568,737, issued Feb. 4, 1986, U.S. Pat. No. 4,587,329, issued May 6, 1986, U.S. Pat. No. 4,713,975, issued Dec. 22, 1987, U.S. Pat. No. 4,871,779, issued Oct. 3, 1989, and U.S. Pat. No. 4,631,337, issued Dec. 23, 1986, discuss the preparation and use of dense star polymers, and U.S. Pat. No. 4,737,550, issued Apr. 12, 1988 and U.S. Pat. No. 4,857,599, issued Aug. 15, 1989, discuss bridged and other modified dense star polymers.

Also, other structural configurations of macromolecular materials that have been disclosed include star/comb-branched polymers, such disclosure being found in U.S. Pat. No. 4,599,400, issued Jul. 8, 1986 and U.S. Pat. No. 4,690, 985, issued Sep. 1, 1987, and finally, rod-shaped dendrimer polymers are disclosed in U.S. Pat. No. 4,694,064, issued Sep. 15, 1987.

The polyamidoamines referred to supra are also disclosed in U.S. Pat. No. 4,758,635, issued Jul. 19, 1988 to Wilson et al.

Hutchins, et al, in U.S. Pat. No. 4,847,328, issued Jul. 11, 1989 and U.S. Pat. No. 4,851,477, issued Jul. 25, 1989, deal with hybrid acrylic-condensation star polymers and Joseph et al in U.S. Pat. No. 4,857,615, issued Aug. 15, 1989, U.S. Pat. No. 4,857,618, issued Aug. 15, 1989, and U.S. Pat. No. 4,906,691, issued Mar. 6, 1990, deal with condensed phase polymers which are linear polymers having regularly, or irregularly, spaced polymeric branches, essentially on the order of a comb structure macromolecule.

An excellent presentation of the structures and chemistries of many such macromoleculer branched assemblies can be found in Tomalia, D. A., Naylor, A. M., and Goddard, W. A. III, Angewandte Chemie, 29/2 (1990), pages 138 to 175.

However, none of the disclosures of the prior art deal with the novel polymers of the instant invention which are non-crosslinked, poly-branched polymers. For simplicity sake, the polymers of the instant-invention can be generally characterized as multiple polymeric branches on multiple polymeric branches.

2 is first grafting and first branching and generation 0;

3 is second grafting and second branching and generation 1;

4 is third grafting and third branching and generation 2;

5 is fourth grafting and fourth branching and generation 3;

6 is $(i+1)^{th}$ grafting and $(i+1)^{th}$ branching and generation i, and 7 is $(i+2)^{th}$ and all iterative grafting and $(i+2)^{th}$ and all interative branching, and generation $(i+1)$ and all subsequent generations.

Figure 2:
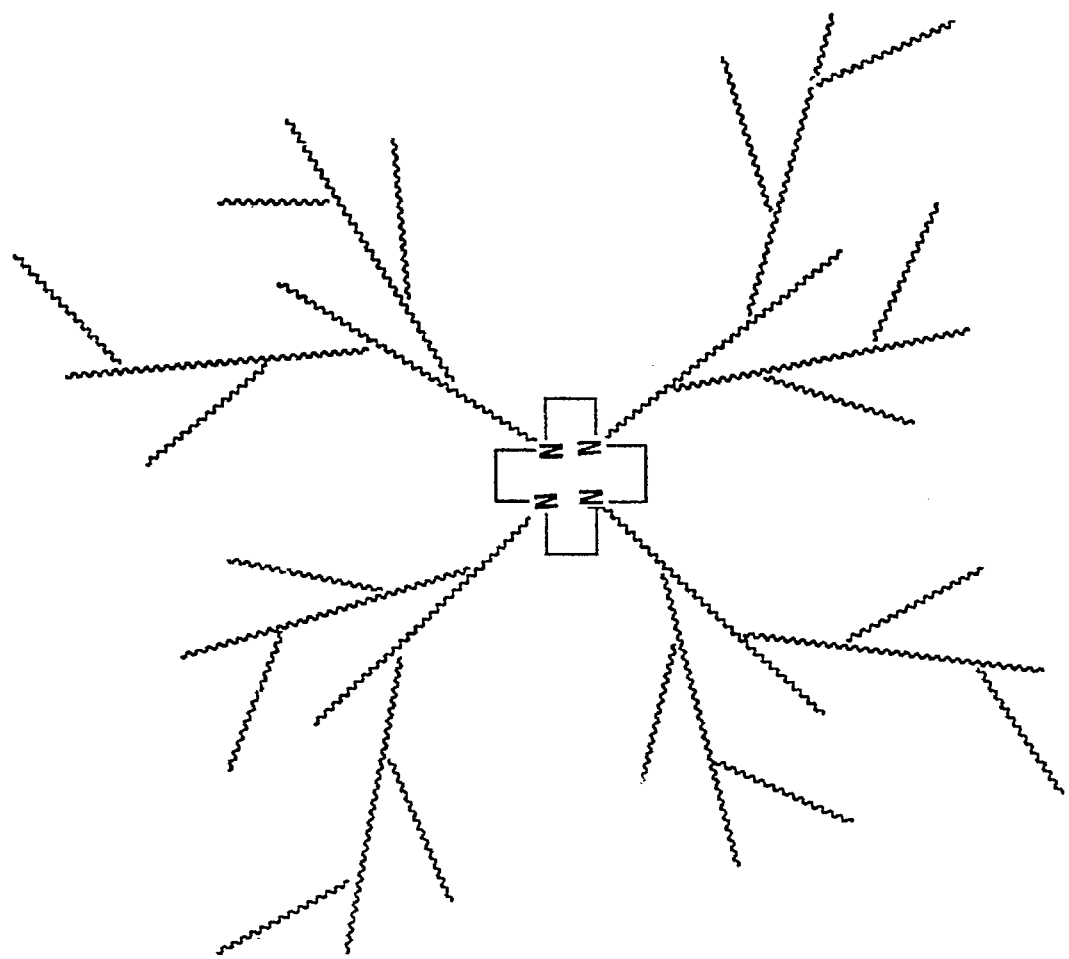
Figure 2:
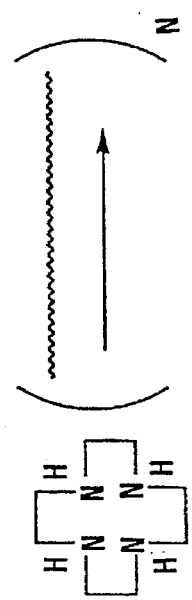
Figure 3:
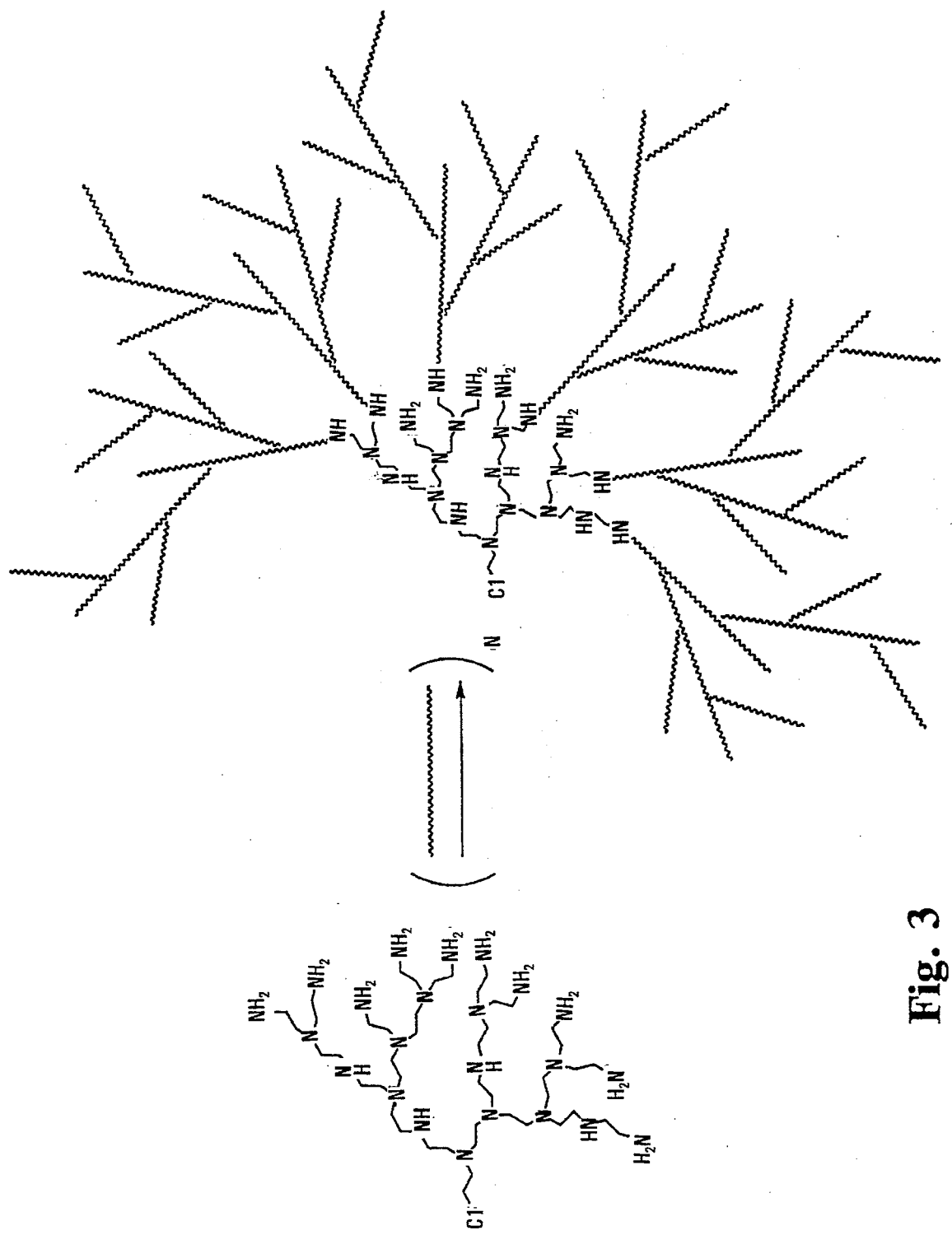

FIG. 2 illustrates the grafting of oligomer branches to cyclen, and the subsequent grafting of branches upon branches; and FIG. 3 shows the grafting of oligomer branches onto a polyethyleneamine dendrimer core, and the subsequent grafting of branches upon branches.

THE INVENTION

Benefits and other perceived advantages are achieved in accord with the present invention which comprises novel non-crosslinked, poly-branched polymers, and methods for manufacturing such polymers. In its broadest scope, this invention deals with poly-branched polymers having at least one branch referred to herein as a "core branch" emanating from a core molecule, said branch being essentially linear, and having at least one end chemically coupled to the core molecule, with the other end of the branch terminating in a group from a molecule used to initiate the reaction by which the branch was prepared, and at least one second branch which is branched from the core branch, said second branch, or branches, being essentially linear, and having at least one end chemically coupled to the core branch, with the other end of the branch terminating in a group selected from a molecule used to prepare the second branch polymer, which when subjected to iterative polymer grafting steps (i.e. generations, which will be delineated further herein), form three-dimensional organizations of ordered organic molecules. These polymers are hereinafter referred to as "comb-burst" structures in that they are prepared from comb-like core molecules, but after subsequent grafting of additional branches pursuant to the processes of this invention, tend to have the appearance in two dimensions of a woven wire fence, which when viewed in three dimensions gives a topology having a starburst-like appearance. Hence, "comb-burst".

This invention therefore comprises compositions of matter comprising non-crosslinked poly-branched polymers having the general formula

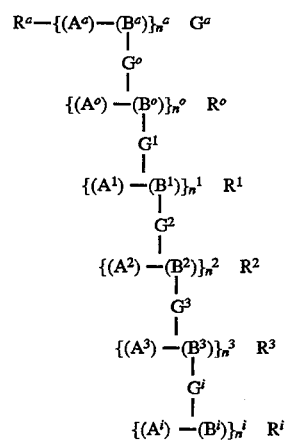

wherein $R^c$ is a non-reactive end group and each $R^o$, $R^1$, $R^2$, $R^3$, and $R^i$ is selected from initiators selected from a group consisting of free radical initiators, cationic initiators, anionic initiators, coordination polymerization initiators and group transfer initiators; (i) represents repetitive linear polymers having the unit formula $\{(A^i)\text{-}(B^i)\}$; $A^c$, $A^o$, $A^1$, $A^2$, $A^3$, and $A^i$ are non-reactive comonomers or, oligomers or polymers formed from a polymerizable monomer, said oligomers or polymers being capable of withstanding the conditions required for preparation of a graft polymer; $B^c$, $B^o$, $B^1$, $B^2$, $B^3$, and $B^i$ are protected or unprotected reactive nucleophilic or electrophilic monomers or, oligomers or polymers formed from a polymerizable monomer, said oligomers or polymers being capable of withstanding the conditions required for preparation of a graft polymer; G is a terminating group or a grafting component and has a value of at least 1; $n^c$ is the degree of polymerization of a core initiator; $n^o$ is the degree of polymerization of a first comb branch; $n^1$ is the degree of polymerization of a first generation comb-burst branch; $n^2$ is the degree of polymerization of a second generation comb-burst branch; $n^3$ is the degree of polymerization of a third generation comb-burst branch, $n^i$ is the degree of polymerization of the $i^{th}$ generation comb-burst polymer having at least one branch point; wherein $n^i \geq 2$ for the case where i=c, o, and 1, and $n^i \geq 2$ if $n^{i-1}$ is > zero, the largest i for which $n^i$ does not equal zero is the total generation level of the polymer wherein the superscripts c, o, 1, 2, 3, and i designate comb-burst generation level; the unit ratio of A units to B units in any $\{(A)\text{-}(B)\}$ segment of the polymer is 0 to 1:100 to 1.

This invention also includes a composition of matter comprising non-crosslinked poly-branched polymers having the general formula

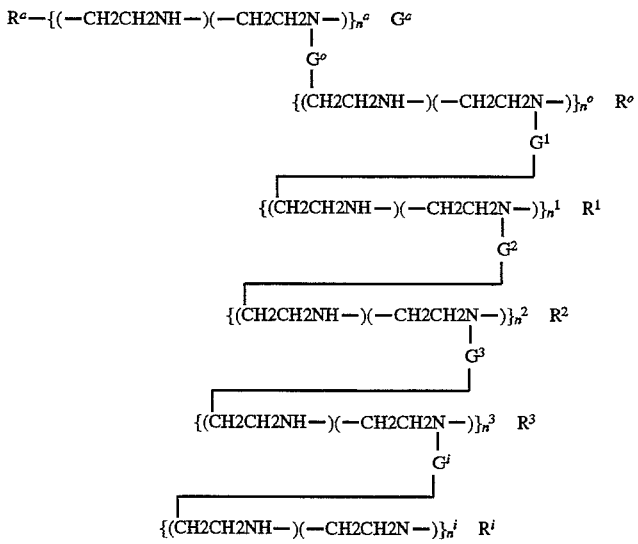

wherein $R^c$ is a non-reactive end group and each $R^o$, $R^1$, $R^2$, $R^3$, and $R^i$ is selected from initiators selected from a group consisting of free radical initiators, cationic initiators, anionic initiators, coordination polymerization initiators and group transfer initiators; (i) represents repetitive linear polymers having the unit formula $\{(-CH2CH2NH-)(-CH2CH2N-)\}$; G is a terminating group or a grafting component and has a value of zero or greater; $n^c$ is the degree of polymerization of a core initiator; $n^o$ is the degree of polymerization of a first comb branch; $n^1$ is the degree of polymerization of a first generation comb-burst branch; $n^2$ is the degree of polymerization of a second generation comb-burst branch; $n^3$ is the degree of polymerization of a third generation comb-burst branch, $n^i$ is the degree of polymerization of the $i^{th}$ generation comb-burst polymer having at least one branch point; wherein $n^i \geq 2$ for the case where i=c, $^o$, and 1, and $n^i > 2$ if $n^{i-1}$ is >zero, the largest i for which $n^i$ does not equal zero is the total generation level of the polymer wherein the superscripts c, $^o$, 1, 2, 3, and i designate comb-burst generation level; the unit ratio of (-CH2CH2NH-) units to (-CH2CH2N-) units in any (-CH2CH2NH-)(-CH2CH2N-) segment of the polymer is 0 to 1:100 to 1.

There does not seem to be any limit to the size of the dendrimers except that dictated by practicality and/or stereochemistry of the molecules formed. Preferred for this invention are values wherein the molecular weight of the molecules is less than about 1,000,000 and more preferred are those having molecular weights of 250,000 or less. Especially preferred are those molecules having a molecular weight of 100,000 or less, and most preferred are those molecules having a molecular weight of about 30,000.

Values of $n_c$ can be from 2 to a value in excess of 300, but a preferred range for the value of $n_c$ is from 2 to 300. Further, the value of $n^o$ can have a range of 2 to a value of in excess of 100, but the preferred value is from 2 to 100. In addition, values of $n^1$, $n^2$, and $n^i$ can be in the range of 1 to a value in excess of 100, but the preferred range is from 1 to 100.

As indicated above, each of $R^o$, $R^1$, $R^2$, $R^3$, and $R^i$ in these inventive polymers is selected as a moiety from a radical initiator, a moiety from a cationic initiator, a moiety from an anionic initiator, coordination polymerization initiator, a group transfer initiator. $R^o$–$R^i$ can be for example hydrogen, an alkyl group, Lewis acids, or the like such materials being known in the art.

The $G^i$ group is the grafting component formed by the reaction of the living end, or a derivative of the living end, of the $i^{th}$ generation oligomer with the reactive groups of the (i-1) generation material. Thus, an anionic oligomer may be reacted directly with an electrophilic precursor generation, or it may be terminated by, for example, a halogen such as chlorine, bromine, or iodine, to create an electrophilic end group for grafting to a nucleophilic precursor. Similarly, a cationic oligomer may be reacted directly with a nucleophilic precursor generation, or terminated with, for example, water, hydrogen sulfide, or an amine to give a nucleophilic end group for reaction with an electrophilic precursor. In the case of $G^c$, the "graft" is to a monofunctional molecule, which may be as simple as quenching the active end with a proton or hydroxide, as would be the case with normal termination of ionic oligomers with water, or trapping with a specific molecule in order to introduce a single desired functional group to the molecule. Other telechelic groups suitable for grafting purposes may be found in Goethals, "Telechelic Polymers"; Syn. Appln., CRC Press (1989).

The oligomeric and polymeric segments of these materials can be homopolymers or copolymers, it being understood that the formulae herein represent bonding of the grafting G groups to either segment A, if it is present, or to segment B, and it being further understood that the grafting to any A segment is at the terminal end of the molecule, any other segment A grafting-would result in the potential for crosslinking the polymers, which is not part of the invention herein. Also, for purposes of this invention, each A segment can be monomeric or, oligomers or polymers formed from polymerizable monomers, the only condition being that the said monomers, oligomers and polymers must be capable of withstanding the conditions required for preparation of subsequent graft junctures. As illustrated in the formulae, the bond from G to the next generation is indicated by a vertical line about halfway between the A segments and the B segments to illustrate that G can be bonded to either A, if it is present, or to B, which is always present in the molecule.

An example of a G group that fits this description would be a urea formed by the reaction of an isocyanate with an amine group. This is formed by the activation of the amines of a poly(vinyl amine) segment with phosgene to create a polyisocyanate precursor molecule which, then, is reacted with an amine terminated poly(vinyl acetamide). The same G group can be formed by treating the poly(vinyl acetamide)

with phosgene to form the telechelic oligomer with isocyanate end group, followed by reaction with the poly(vinyl amine) precursor molecule.

An example using the A group bonded to the G group would be the use of a copolymer of ethyl oxazoline and ethylene oxide. The hydroxyl group on oxyethylene is the terminal group on the reactive oligomer segment. Activation of the hydroxyl group with phosgene gives a chloroformate which is reacted with the amine of a poly(ethyleneimine) segment on the precursor generation to form a urethane. Thus, the A group of the reactive oligomer is the "unreactive" oxyethylene and the B group is the masked iminoethylene, N-propionyl iminoethylene.

The range of possible G groups is limited only by the types of coupling reactions that are possible. In addition to ureas and urethanes, imide, thiourea, thiocarbamate, and anhydride linkages are readily available from similar reagents. Precursor molecules containing olefins that result from polymerization or copolymerization of butadiene or ring opening metathesis polymerization of cyclic olefins can be activated by halogenation for subsequent reaction with a nucleophilic end group, or reacted directly with mercaptans via radical addition, or be coupled with a silane end group via catalyzed hydrosilylation methods. Ether and ester linkages can be derived from hydroxyl groups on either the precursor molecule or the reactive oligomer end group.

Segments of A include for example, $-CH_2CH_2-$, $-CH_2CH=CHCH_2-$, $-CH_2C(CH_2)_2-$, $-CH_2CH(CN)-$,

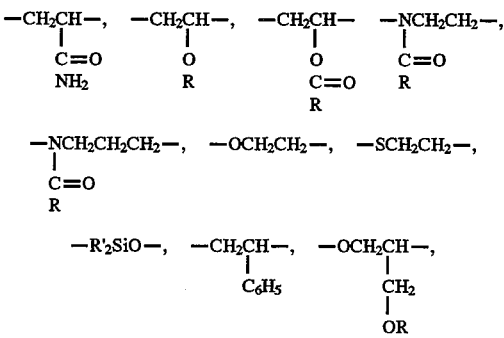

wherein R' is an alkyl group of 1 to 4 carbon atoms, aryls, arylalkyl, hydrogen, or carboalkoxy and R is an alkyl group of 1 to 4 carbon atoms, aryls, or hydrogen;

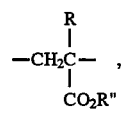

wherein R has the same meaning as set forth above, and wherein R" can be an alkyl group of 1 to 4 carbon atoms. Preferred as A segments are $-CH_2CH_2-$,

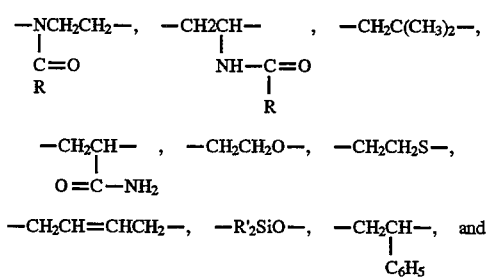

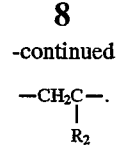

Most preferred are the A segments

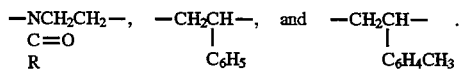

Examples of the B segment can be monomeric, or oligomers or polymers formed from polymerizable monomers, wherein said monomers, oligomers and polymers must be capable of withstanding the conditions required for preparation of a graft polymer and further, the B segments must contain at least one unit which is nucleophilic or electrophilic in character.

The groups B contain the reactive sites to which the oligomers may be grafted. In many cases, these groups may need to be present in latent or masked form if they would otherwise be incompatible with the oligomerization process. For example, polymerization of ethyleneimine leads to highly branched polyethyleneimine oligomers which are not useful for this invention because the secondary amines formed are also reactive under the polymarization conditions. Oxazoline polymerization leads to linear polyethyleneimine in a protected form, and the secondary amines can be unmasked for grafting by hydrolysis. For alkylene oxide oligomerizations, hydroxyl groups intended for use as future graft sites would need to be masked as, for example, an ether to preclude the possibility of forming highly cross-linked gel systems. An example of a latent reactive site would be an alcohol group of a polyol which would require activation by conversion to a halide or sulfonate to allow reaction with anionic oligomer.

Thus, B as a nucleophile can be selected from such groups as

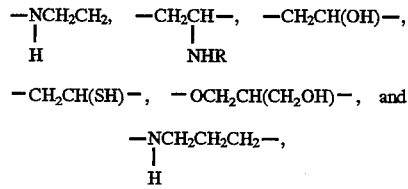

while B as an electrophile can be selected from such groups as

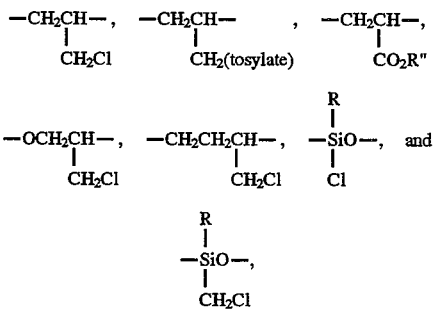

wherein R and R" have the meanings set forth above.

It should be understood that homopolymers consist of only the B segment, while copolymers can be had by combining the B segments with the A segments. Copolymers can also be prepared by using different monomers for the B segment of different generations, for example $B^1$ being different from $B^2$.

The inventors herein contemplate that for purposes of this invention, there must be at least one B segment and therefore the ratio of A segments to B segments ranges from 0 to 1 to 100 to 1.

This invention also comprises a process for preparing non-crosslinked poly-branched polymers having the general formula

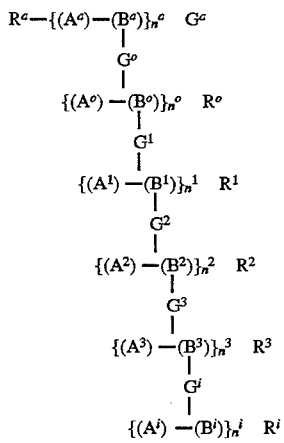

wherein $R^c$ is a non-reactive end group and wherein each $R^o$, $R^1$, $R^2$, $R^3$, and $R^i$ is selected from initiator types selected from a group consisting of free radical initiators, cationic initiators, anionic initiators, coordination polymerization initiators, and group transfer initiators; (i) represents repetitive linear polymers having the unit formula $\{(A^i)-(B^i)\}$; $A^c$, $A^o$, $A^1$, $A^2$, $A^3$, and $A^i$ are non-reactive comonomers or, oligomers or polymers formed from a polymerizable monomer, said oligomers or polymers being capable of withstanding the conditions required for preparation of a graft polymer; $B^c$, $B^o$, $B^1$, $B^2$, $B^3$, and $B^i$ are protected or unprotected reactive nucleophilic or electrophilic monomers or, oligomers or polymers formed from a polymerizable monomer, said oligomers or polymers being capable of withstanding the conditions required for preparation of a graft polymer; G is a terminating group or a grafting component having a value of at least one; $n^c$ is the degree of polymerization of a core initiator; $n^o$ is the degree of polymerization of a first comb branch; $n^1$ is the degree of polymerization of a first generation comb-burst branch; $n^2$ is the degree of polymerization of a second generation comb-burst branch; $n^3$ is the degree of polymerization of a third generation comb-burst branch, $n^i$ is the degree of polymerization of the $i^{th}$ generation comb-burst polymer having at least one branch point; wherein $n^i \geq 2$ for the case where i=c, $^o$, and 1 and $n^i \geq 2$ if $n^{i-1}$ is >zero, the largest i for which $n^i$ does not equal zero is the total generation level of the polymer wherein the superscripts c, $^o$, 1, 2, 3, and i designate comb-burst generation level; the unit ratio of A units to B units in any $\{(A)-(B)\}$ segment of the polymer is 0 to 1:100 to 1, the process comprising (I) forming a linear initiator core having at least one reactive site and having the general formula $R^c\text{-}\{(A^c)\text{-}(B^c)\}_{n^c}\ G^c$; (II) reacting all or part of the sites ($B^c$) of (I) with a reactive polymer having the unit formula $G^o\{(A^o)\text{-}(B^o)\}_{n^o}\cdot R^0$ to form multiple branches that contain at least one reactive site on each branch using protection-deprotection reactions to ensure that the unit formula $G^o\{(A^o)\text{-}(B^o)\}_{n^o}\cdot R^o$ reacts only with ($B^c$) sites of (I) and that no reactions occur at the reactive sites $B^o$; (III) repeat (II) sequentially to form successive generations of reactive branches to give the desired non-crosslinked poly-branched polymers.

This invention further comprises a process for preparing non-crosslinked poly-branched polymers having the general formula

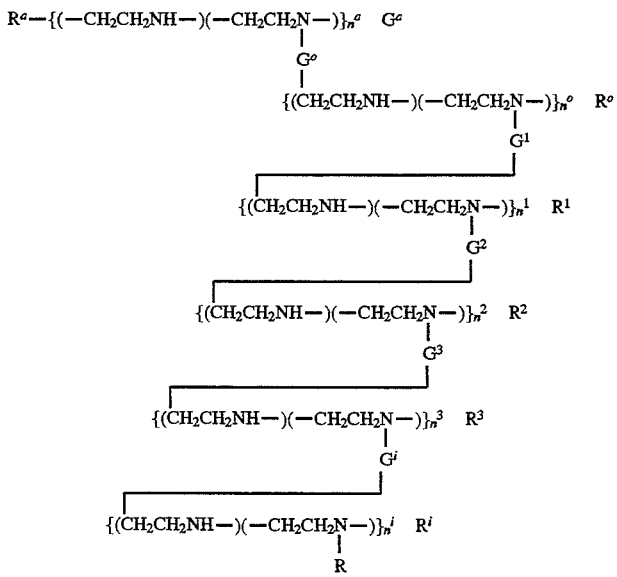

wherein the values of the symbols, superscripts, and subscripts are set forth above.

It should be noted by those skilled in the art that the polymer requires an initiator core (initiator core molecule). This initiator core may or may not be a "living polymer" or "living oligomer", which oligomers and/or polymers are generally known to those skilled in the art. "Living systems" are preferred in order to control polydispersity of the comb-burst dendrimers. Using specific chemistry, the inventors herein can explain this aspect of the invention beginning with reference to "Polymeric Amines And Ammonium Salts", edited by E. J. Goethals, Pergamon Press,.(1980), with especial reference to pages 55 et seq. wherein there is taught one method of producing living polymers in a paper entitled "Linear Polyalkylenimines", Saegusa, T. and Kobayashi, S.

Using the example of Saegusa, page 58, one can observe that an initiator such as methyl iodide is first reacted with an oxazoline in the following sequence to give an oligomeric "living oligomer" having, in this case, two protected reactive sites designated as $$-NCH_2CH_2-:$$
$$|$$
$$C=O$$
$$H$$

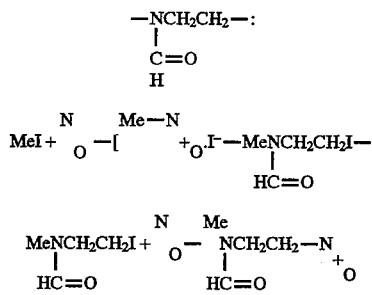

that is,

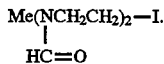

Figure 1:
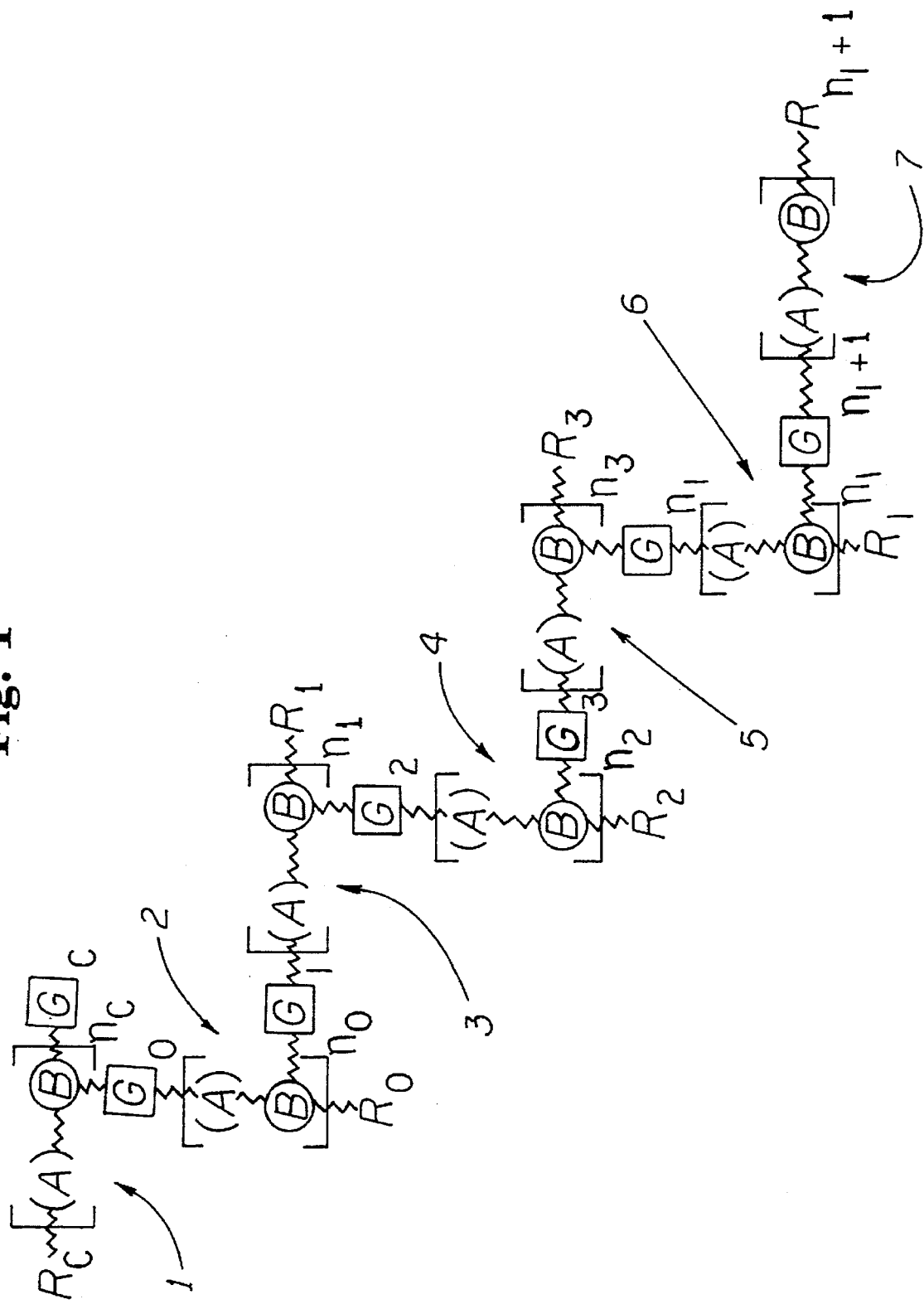
FIG. 1 is a schematic in two dimensions of the polymer configuration of the polymers of the instant invention wherein 1 is the initiator core (initiator core molecule)

With further reference to FIG. 1 of the instant invention, the initiator core in the specific case described just above would be shown in FIG. 1 as $R^c(B^a)_{na}$ $G^a$; where $R^a$ is methyl and $G^c$ is as described above.

Reaction sequences are then chosen to deprotect the nitrogen groups so that each of the two reactive sites adds a reactant possessing its own, new reactive site, or sites, which introduces multiplicity, to obtain a "dendrimer" $-\{(A^c)-(B^c)\}_n-R^c$ of generation 0 (see FIG. 1), wherein "dendrimer" has the same or similar meaning as that used by Tomalia, et. al. in the article referenced supra. As can be observed from the reaction sequence set forth above, this process requires that protection-deprotection strategies are used to ensure that the reactant reacts with all reactive ($B^c$) sites, but does not react any ($B^o$) sites. Protection-deprotection strategies are generally known to those skilled in the art and great detail does not have to be set forth, herein. Suffice it to suggest that the living oligomer set forth above has the protective group

on each nitrogen of the oligomer whereupon the oligomer is then hydrolyzed with an acid to give polymeric units having reactive amine groups i.e.

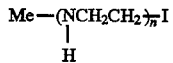

which are then used as the reactive sites to form the next generation, it being understood that the reactive sites of the polymer being grafted to the amine groups are protected before this reaction takes place, and that they too are hydrolyzed after the grafting reaction to give additional reactive sites for the next generation of branching. Additional iterative sequences involving addition of new reactants having reactive sites is then undertaken in order to add branches onto branches to form the poly-branched polymer of this invention until the polymers will not form due to steric hinderence referred to as comb-burst dense packing. The article by Tomalia, et al, referenced supra sets forth such technical terms.

One of the inventive processes used to prepare polymers of this invention relies on the polymerization of 2-ethyl-2-oxazoline. Methyl p-toluenesulfonate has been shown to polymerize oxazolines and the polymerization mechanism has been determined to be cationic, producing a "living polymer". This allows the preparation of polymer samples with well defined molecular weight and low polydispersity. The end of the growing polymer chain contains an oxazolinium ion as disclosed above, that can be trapped by a variety of nucleophiles. To graft the living poly(2-ethyl-2-oxazoline) chains, they are terminated with the secondary amine groups contained on linear poly(ethyleneimine) (LPEI). After grafting onto the linear poly(ethyleneimine) has been accomplished, hydrolysis of the poly(2-ethyl-2-oxazoline) grafts will generate poly(ethyleneimine) branches. This allows further living poly(2-ethyl-2-oxazoline) chains to be grafted onto the poly(ethyleneimine) branches. Repetition of the grafting and hydrolysis forms the inventive polymers with the structures shown herein.

FIGS. 2 and 3 and Examples 31 and 32 below illustrate branching "0" generation branches onto cores comprising ring compounds and dendrimers respectively. In FIG. 2, branches which can be generated in the manner described above are attached to the four nitrogens in the ring compound 1,4,7,10-tetraazacyclododecane (cyclen), much as they are grafted to the nitrogens of a polyethyleneimine core molecule as discussed above. First generation branches are then grafted upon the "0" generation branches, second generation branches are grafted upon the first generation branches, etc. as discussed above.

In FIG. 3, "0" generation branches are grafted to the surface nitrogens of a hyper-terminal-branched or dendrimer core molecule, specifically, a second generation polyethyleneamine. At the generation 2 level (designating the first generation as generation 0), such hyper-terminally-branched molecules are typically referred to as "dendrimers." Hyper-terminal-branched or dendrimer cores can be prepared in various manners known to those skilled in the art including without limitation by the techniques disclosed in U.S. Pat. No. 4,507,466 entitled "DENSE STAR POLYMER BRANCHES HAVING CORE, CORE BRANCHES, TERMINAL GROUPS," U.S. Pat. No. 4,558,120 entitled "DENSE STAR POLYMER," U.S. Pat. No. 4,568,737 entitled "DENSE STAR POLYMERS AND DENDRIMER," U.S. Pat. No. 4,587,329 entitled "DENSE STAR POLYMER HAVING TWO-DIMENSIONAL MOLECULAR DIAMETER," U.S. Pat. No. 4,631,337 entitled "HYDROLYTICALLY STATE DENSE STAR POLYAMINE," U.S. Pat. No. 4,737,550 entitled "BRIDGED DENSE STAR POLYMER," U.S. Pat. No. 4,599,400 entitled "STAR/COMB-BRANCH POLYAMIDE," U.S. Pat. No. 4,690,985 entitled "STAR/COMB-BRANCHED POLYAMINE," U.S. Pat. No. 4,694,064 entitled "ROD-SHAPED DENDRIMER," and U.S. Pat. No. 4,857,599 entitled "MODIFIED DENSE STAR POLYMERS." Similarly, any of the dendrimer molecules described in said patents could be used as the hyper-branched dendrimer core to which oligomer branches are grafted in reiterative fashion in accordance with the present invention. One need only develop an appropriate strategy for attaching the oligomer branches to the surface moieties of such hyper-branched cores, and various alternatives will be apparent to those of ordinary skill in the art.

For purposes of clarifying terminology, it should be noted that the hyper-terminal-branched core molecule disclosed in FIG. 3 and in Example 32, and those disclosed in the United States patents discussed above are built by reiterative terminal branching rather than reiterative comb-branching. That is to say, one attaches subsequent generation branches to the terminal moieties of a previous generation, thus limiting the degree of branching to the functionality of the previous generation terminal moiety, which would typically be two or three. In contrast by branching oligomers upon prior generation oligomer branches in accordance with the present invention, one can dramatically increase the degree of branching from generation to generation, and indeed can vary the degree of branching from generation to generation.

In another preferred embodiment process, the non-crosslinked poly-branched polymers, or hyper-comb-branched polymers, are produced in a remarkably low number of iterations by utilizing a particular combination of process parameters and reactants having certain characteristics. It has been surprisingly discovered that hyper-comb-branched polymers having a molecular weight of about 1 million and up to about 10 million or even higher can be produced in only several reaction iterations by this preferred embodiment process. A hyper-comb-branched polymer product having a molecular weight exceeding 10 million was formed in only 4 iterations from a core of linear PEI 20, and side chains of PEOX 10 for the first iteration and PEOX 100 for the next 3 iterations, by the preferred embodiment process described below. It is contemplated that hyper-comb-branched polymers having a molecular weight ranging from about 10 million to about 50 million could be produced in about 4 iterations. It is further contemplated that even higher molecular weight products could be formed such as products having a molecular weight of about 100 million or more by continuing the iterations. Such remarkably high molecular weight polymers are produced in a surprisingly few number of iterations primarily by utilizing longer side chains, a particular grafting ratio, shorter reaction time periods, and utilizing a proton trap to increase grafting yields and prevent chain scission of the comb-branched intermediates and resulting hyper-comb-branched polymer product. In another aspect of the preferred embodiment process, a novel separation technique is provided for separating a hyper-comb-branched polymer product from a reaction mixture, that is both economical and rapid.

The present inventors have discovered that grafting yields may be significantly increased by utilizing a particular grafting ratio of living chain ends to secondary mines, and in some instances, by also employing a proton scavenger during grafting operations. Prior to the present discovery, when producing comb-branched polymers from PEI cores and PEOX 5 to PEOX 10 as grafting chains at a grafting ratio of 0.3 living chain ends per secondary amine, grafting yields typically ranged from about 10% to about 15%. In the present preferred process, it is preferred to utilizing a grafting ratio of from about 0.8 to about 1.2 living chain ends per secondary mine, and most preferred to utilizing a grafting ratio of about 1:1 of living chain ends to secondary amines. These grafting ratios result in significantly improved grafting yields.

At these grafting ratios, i.e. about 0.8 to about 1.2:1, it has been found that it is also beneficial to utilize a proton scavenger during grafting to trap or scavenge protons which are generated during grafting, such as when a living PEOX chain is grafted onto a secondary amine such as PEI. Without such scavengers, expelled protons are transferred to basic secondary amine sites along the PEI polymer backbone, thereby blocking and thus rendering those sites inaccessible for further grafting. In the preferred embodiment process, the use of a proton scavenger and a grafting ratio of about 1:1 has been found to significantly increase grafting efficiency, such as up to about 75% to 95% when grafting PEOX 5 or PEOX 10 branches onto a PEI core.

Proton scavengers may comprise nearly any suitable base that is compatible with the core and side chain reactants. A preferred proton scavenger for use when grafting PEOX chains onto PEI is a relatively hindered, tertiary mine such as i-$Pr_2$NEt. However, it is contemplated that a wide array of suitable bases could be utilized instead of, or in addition to i-$Pr_2$NEt, such as triisobutylamine, triisooctylamine and triethylamine. The proton scavenger is preferably utilized in the grafting mixture in a concentration of from at least about 1 to about 2 equivalents of the proton scavenger for every living or reactive chain end. It is envisioned that even higher ratios may be utilized in certain instances.

As previously noted, the remarkably high molecular weight polymeric products are produced in a surprisingly few number of iterations by increasing grafting yield, and by preventing chain scission of the comb-branched intermediates and resulting hyper-comb-branched polymer products. In the case of utilizing PEOX and PEI to produce a hyper-comb-branched polymer, chain scission often occurs when there exists an excess of chain ends to secondary mines in the reaction environment. An excess of chain ends to secondary mines promotes the formation of quaternary amines along the polymer backbone, which readily undergo Hofmann degradation to produce undesirable lower molecular weight fragments upon heating.

The present inventors have discovered that chain scission may be essentially prevented or significantly minimized by employing one or more of the following practices: (a) utilizing shorter reaction periods, (b) utilizing relatively long chains for grafting onto polymer backbones, (c) ensuring that NaOH or other salts are completely removed, or nearly so, from the reaction mixture(s) throughout the various stages of the process, and (d) ensuring that the resulting hyper-comb-branched product is maintained at relatively low temperatures and not exposed to high temperatures. It is preferred to employ all of these practices to prevent chain scission, and most preferred to employ all of these practices in conjunction with utilizing the previously described grafting ratios and proton scavenger during grafting operations to increase grafting yields.

Shorter reaction periods are utilized for both polymerization of the reactants, e.g. core and branches, and grafting operations in the preferred embodiment process since shorter reaction periods have been found to reduce the tendency for quaternary amines to be formed. Quaternary amines, as previously noted, are prone to undergo Hofmann degradation and thereby cause chain scission. When forming PEOX side chains from PEOX 10 or PEOX 20, for later use in preparing hyper-comb-branched polymers, it is preferred to utilize a time period of less than about 5 hours for the polymerization of PEOX. When forming PEOX side chains from PEOX 100, longer time periods may be required such as up to about 10 hours. It is particularly preferred to employ relatively short time periods during grafting operations, such as a grafting reaction time of less than about 1 hour for grafting polymerized PEOX chains onto a PEI core.

In addition to forming side chains from PEOX, it is possible to utilize a wide array of monomer units such as, but not limited to any 2-, 4-, or 5-substituted oxazoline;

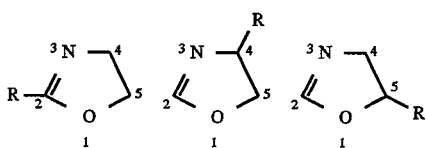

any 2-unsubstituted 5,6-dihydro-4H-1,3-oxazines;

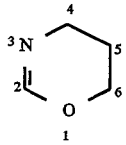

any 2-substituted 5,6-dihydro-4H-1,3-oxazines;

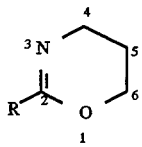

or any block copolymers containing 5,6-dihydro-4H-1,3-oxazines and 2-alkyloxazolines. Hyper-comb-branched polypropyleneimine polymer obtained by hydrolysis of poly(5,6-dihydro-4H-1,3-oxazines), both 2-substituted and 2-unsubstituted, were found to exhibit a relatively high degree of thermal stability as compared to those having PEI side chains.

The tendency for chain scission is further reduced by utilizing relatively long chains for grafting onto a polymer backbone. Once a long side chain is grafted onto a secondary amine to generate a tertiary amine site along the polymer backbone, it is nearly impossible to introduce another chain, particularly another long chain, at this tertiary amine site due to steric inhibition. In the case of forming hyper-comb-branched polymers from PEOX and PEI, it has been discovered that the preferred length for PEOX side chains or branches are at least about 50 monomer units, and most preferably at least about 100 monomer units.

In another preferred embodiment, relatively short chains are utilized during the early stages in forming the hyper-comb-branched product, i.e., generation 0, (G0) and relatively long side chains are utilized during later stages, i.e., generations 1 (G1) and above. This practice has been found to increase interior branching density, and reduce the previously described tendency for chain scission to occur at higher generations.

Chain scission may also occur after initial formation of the poly-branched polymer or hyper-comb-branched polymer, such as during or after neutralization of the hydrolyzed polymer product. After formation of the comb-branched polymer product and addition of acid to hydrolyze the product, the polymer product is neutralized and separated from the reaction mixture by adding base to form an oily layer containing the polymer product. This is typically accomplished by adding a base such as NaOH followed by heating until an oily layer separates from the mixture, that layer containing the high molecular weight product. The oily layer is then cooled to harden or solidify it, wherein it can be readily removed. It has been discovered that after neutralization with NaOH, the PEI moieties in the polymer product tend to chelate the sodium cations, thereby freeing hydroxyl ions and increasing the pH of the environment, and further promoting Hofmann degradation of any quaternary amines present upon heating, which in turn leads to chain scission. Additionally, unwanted amounts of NaOH or other salts may contaminate the reactants used in forming the polymer product, such as linear PEI. Such contamination can later promote chain scission. Removal of NaOH or other salts from the poly-branched polymer, and/or from the components used to form such product, has been discovered to reduce the tendency of chain scission of the poly-branched or hyper-comb-branched polymer. NaOH or other salts may be removed from the reaction mixture at various points of the process by a wide variety of techniques such as exhaustive washing with water of precipitated polymer product or of the reactants used to form the polymer product which are believed to contain NaOH, and then dissolving the polymer product in toluene, in which NaOH is insoluble, heating to remove water by azeotropic distillation, then filtering or otherwise separating the hot polymer product from the NaOH and/or other salts. The various points of the process in which it is desirable to remove NaOH or any other salts include the stage in which the reactants are polymerized to form chains for subsequent grafting onto the polymer core or backbone, and the stage in which the grafting occurs.

Chain scission is also minimized in accordance with the preferred embodiment process by not exposing the resulting poly-branched or hyper-comb-branched polymer product to temperatures that are significantly above room temperature, such as when drying by ovens in which case, temperatures of 100° C. or more are often reached. Conventional drying procedures in which PEI polymer was dried at 80° C. in an oil bath and under vacuum overnight were found to degrade the comb-branched polymer into undesirable numerous smaller fragments. Thus, it is preferred that PHI poly-branched or hyper-comb-branched polymer product is dried at temperatures less than about 60° C., and it is most preferred that the PEI product be stored at room temperatures, i.e. about 20° C. It has been found that PEOX-PEI comb-branched polymers exhibit greater thermal stability than PEI comb-branched polymers. Thus, it is preferred to store hyper-comb-branched polymers in the PEOX-PEI stage and hydrolyze the polymers to PEI hyper-comb-branched polymers prior to use.

In another aspect of the preferred embodiment process, a novel separation technique is provided for separating a poly-branched or hyper-comb-branched polymer product from a reaction mixture containing lower molecular weight products that is both economical and rapid. Currently known techniques for separating high molecular weight, highly branched polymers from reaction mixtures generally involve some type of ultrafiltration process. Ultrafiltration, although satisfactory in many respects, is undesirable in view of the relative high cost of ultrafiltration equipment and the inefficiencies associated with separating high molecular weight products from undesired low molecular weight products. The present inventors have discovered a separation technique, whereby ultrafiltration is avoided and the polymer product is separated by a polymer refractionation technique.

The preferred polymer refractionation technique is performed by separation of hyper-comb-branched polymer product from a reaction mixture comprising the product and unwanted lower molecular weight components at the PEOX-PEI stage, by a first addition of an alcohol solvent in which both high molecular weight and low molecular weight products are soluble, and a second incremental addition of a poor solvent in which the high molecular weight product is less soluble than the unwanted low molecular components. Addition of the poor solvent to the alcohol and dissolved components causes the high molecular weight polymer product to precipitate from solution. Examples of suitable poor solvents include, but are not limited to, diethyl ether or other ether-based solvents and hexane.

An example of the preferred refractionation technique is as follows. An alcohol solvent such as methanol is added to the reaction mixture, until all of the components in the mixture, including unwanted low molecular weight components and the high molecular weight polymer product, are dissolved and are in solution. Then, a poor solvent such as diethyl ether, is incrementally added to preferentially precipitate the desired high molecular weight components from the alcohol phase containing the low molecular weight products. Poor solvent is added until all, or substantially all, of the high molecular weight product is in the precipitate. Periodically, the resulting oil sludge bottom product, i.e. precipitate, and/or top layer containing the dissolved low molecular weight products are analyzed for the presence of the high molecular weight polymer product. Analysis may be performed by SEC (size exclusion chromatography) methods. Once the high molecular weight polymer product no longer precipitates from the resulting mixture of alcohol solvent, poor solvent, and low molecular weight components, and thus is in the precipitate, addition of the poor solvent is halted. The mixture remaining above the precipitate and containing the low molecular weight product, is then removed. The high molecular weight poly-branched or hyper-comb-branched product remains in the bottom precipitate layer and can be redissolved in water and subsequently dried by lyophilization.

EXAMPLE 1

A 250 ml one-necked round-bottomed flask equipped with a magnetic stirring bar and a Dean-Stark trap that was surmounted with a reflux condenser was charged with 2.84 gm (15.3 mmole) of methyl tosylate and 125 ml of toluene. The mixture was heated at reflux and solvent was collected until all water had been removed. At this time, 30.0 gm (303 mmoles) of freshly distilled 2-ethyl-2-oxazoline was added all at once and the mixture was refluxed for approximately 4 hours. During this time, in a separate flask, 1.64 gm (38.1 mmole of repeat units) of linear poly(ethyleneimine) (LPEI) was azeotropically dried with toluene. When the poly (ethyleneimine) was dry it was added to the round-bottomed flask containing the oxazoline oligomer and then allowed to reflux for an additional 3 hours. Any ungrafted living poly(2-ethyl-2-oxazoline) chains were neutralized by the addition of 2.0 ml of water with refluxing for an additional 1 hour. Toluene was removed under reduced pressure to leave a yellowish oily solid that was dissolved in chloroform and precipitated dropwise into diethyl ether. The yellow solid was filtered from solution and dried overnight in a vacuum oven to yield 29.7 gm (94% yield) of grafted poly(2-ethyl-2-oxazoline) (PEOX) as a yellow powder.

EXAMPLE 2

Into a 500 ml one-necked round-bottomed flask was placed 21.6 gm of the oxazoline from example 1 and 350 ml of water. When the polymer had completely dissolved, 35 ml of concentrated sulfuric acid was added. The flask was equipped with a distillation head and the mixture was heated at reflux and distillate was collected until propionic acid could not be detected. Water was added to the distilling pot when the volume was reduced to less than approximately 75 ml. Upon removal of the propionic acid the distillation head was replaced with a reflux condenser surmounted with a pressure equalized addition funnel charged with 5N NaOH. The base was slowly dripped into the reaction mixture maintained at reflux. When the pH of the reaction mixture was approximately 12, heating was discontinued. While standing at room temperature a solid formed at the surface of the aqueous mixture. This solid was removed and placed in a 250 ml round-bottomed flask with 175 ml of toluene. The water was removed from the water-toluene azeotrope by distillation. When water removal was complete, the solid became soluble in the refluxing toluene. The hot toluene solution was poured into a 250 ml round-bottomed flask leaving behind insoluble salts. Toluene was removed under reduced pressure to leave a brownish, waxy solid. The sample was dried for approximately 24 hours under vacuum to give 9.14 gm (97% yield) of polymer sample.

EXAMPLE 3

Using the general method of Example 2, hydrolysis of the graft polymers, was carried out on a separate batch of the graft polymers in the following manner. Five grams (5.0 gm) of the graft copolymer were placed in a 250 ml round-bottomed flask with 100 ml of water and 10 gm of sulfuric acid. The flask was heated with a heating mantle to give a slow distillation of the propionic acid/water azeotrope. The distillation was continued for 2 days, with water being added as necessary to maintain the reaction volume. Approximately 200 ml of distillate was collected over the course of the hydrolysis. The heating was discontinued and 50% NaOH was added slowly to bring the pH to 10. The free polyamine was insoluble in the saturated salt solution, giving a separate phase on top of the aqueous solution. The phases were separated and the polyamine was placed in a 250 ml round-bottomed flask. One hundred fifty ml of toluene was added and a Dean-Stark trap was attached. After reflux overnight (about 16 hours), no more water was being removed and the polyamine had dissolved in the hot toluene. The hot solution was filtered and the solvent was removed from the filtrate using vacuum and agitation to give branched poly(ethyleneimine) weighing 2.2 gm (100% of theory) as an orange oil. The $^{13}$C-NMR spectrum showed a peak for linear poly(ethyleneimine) (49.4 ppm/intensity 8075), residual unhydrolyzed propionamide (9.5 ppm/intensity 156),(26.3 ppm/intensity 180), and primary amine end group (41.7 ppm/intensity 61). No peak for a hydroxy terminal group was observed. While the intensities may not be interpreted as a quantitative measure of the groups present, qualitatively, hydrolysis was 80 to 90% complete and grafting was complete within the limits of detection.

EXAMPLE 4

A 2 liter, 3-necked, round-bottomed, glass flask was used with a shaft driven stirrer, instead of magnetic stirring. The initial loading was: water—250 ml, material prepared essentially by the method of example 3—125 gm, sulfuric acid—150 gm. Additional sulfuric acid, 100 gm was added halfway through the hydrolysis to improve solubility. Internal flask temperature was monitored and a solenoid valve was rigged to add water whenever the temperature rose above 107° C. Thus, constant attention was not necessary and the distillation could be left unattended overnight. The heating mantle was also set to shut off at the same temperature so that the flask would not overheat if the water reservoir ran out of water. After 2 days of continuous distillation, 1.6 liters of distillate was collected. The reaction mixture was neutralized and the polymer phase was separated. The crude polymer was purified by dissolving in hot water (1 liter) and precipitated by slow addition to cold water. After two precipitations, the supernatant solution was neutral to Hydrion® paper. The resulting hydrated polymer was dehydrated via toluene azeotrope as described above to give LPEI (51 gm 94% yield). The $^{13}$C-NMR spectrum showed LPEI with residual amide carbon intensities 0.5% of the LPEI intensity. Primary amine end group intensity was 0.4% of the LPEI intensity.

EXAMPLE 5

Into a 250 ml round-bottomed glass flask was placed p-toluenesulfonic acid monohydrate (2.0 gm, 11 mmole) and toluene (100 ml). A Dean-Stark trap was attached and the mixture was heated at reflux until water removal was complete. Ethyl oxazoline (10 gm, 100 mmole) was added all at once and the reflux was continued for 2 hours. LPEI (1.0 gm, 23 meq.) was placed in toluene (25 ml) and the mixture was heated to boiling to dissolve the polymer and azeotropically remove trace water in the polymer. The hot LPEI solution was added all at once, to the cloudy oligomer suspension. An orange oil began to precipitate immediately. After 1 hour at reflux, the mixture was cooled and the solvent stripped using vacuum. The residue was dissolved in $CH_2Cl_2$ (40 ml) and precipitated by a slow addition to ether (500 ml). The solid was collected by filtration and dried in a vacuum oven at 40° to 50° C. to give the grafted polymer (12 gm, 92% yield) as a yellow powder. At higher M/I ratios, the oligomerization time had to be increased to allow complete coversion of the ethyl oxazoline. For example, intermediated degree of polymerization runs (M/I=200, olig. time=3 hours. or M/I=400, olig. time=6 hours) had low yields due to incomplete conversion. Increasing the reaction time to 12 hours and 24 hours respectively, gave higher conversions and yields. The highest M/I (1000) run, had an oligomerization time of 36 hours, which was not long enough for complete conversion. This gave a material with actual oligomer dp of 700. The $^{13}$C-NMR spectrum of the poly-branched polymer derived from this material showed a peak for primary amine end groups which was approaching the limits of detection for the signal/noise ratio. No hydroxyl terminal group was detectable.

EXAMPLE 6

Preparation of Morpholine Terminated Linear Polyethyleneimine Having a Degree Of Polymerization (dp) of 20.

A mixture of Methyltosylate (7.46 g, 40 mmol) in 200 ml of toluene was azetroped to dryness with a Dean-Stark trap for about 10 to 15 minutes. To this mixture which had cooled to about 90° C. was added ethyl oxazoline (79.3 g, 800 mmol) and the mixture was refluxed for 18 hours. To this mixture which had been cooled to about 90° C. was added morpholine (14 g, 161 mmol). This mixture was refluxed for 16 hours. This mixture was evaporated of volatiles on a rotary evaporator. This crude mixture was hydrolyzed with 400 ml of 50% $H_2SO_4$ by. azeotroping the water-propionic acid mixture with a Dean-Stark trap until about 500 ml were collected or until the pH of the distillate was neutral. This hot mixture was slowly poured into a 50% KOH mixture under an atmosphere of $N_2$. The resulting heterogenous mixture was made homogeneous by heating to reflux. The product floated to the top of this mixture as a clear liquid. This hot mixtrue was allowed to cool under $N_2$ to room temperature. The solid cake that formed on the surface of this mixture was dissolved in 600 ml of deionized water by heating to reflux, allowed to cool and ultracentrifuged (8000 rpm) for 10 minutes. The clear liquid was decanted and the remaining white solid-water mixture was mixed with toluene. This mixture was azeotroped of water to form a dry toluene-LPEI mixture. The toluene was removed, from this mixture by a rotary evapaorator followed by high vacuum (0.2 mm Hg) at 80° C. for 2 hours to give 34 g (88%) yield) of the title compound.

EXAMPLE 7

Preparation of Comb-Branched PEI Wherein $N_c$ is 20, $N_b$ is 5 and G is zero.

A mixture of Methyl tosylate (MeTOs) (3.7 g 20 mmol) in 50 ml of toluene was azeotroped to dryness with a Dean-Stark trap under nitrogen for 10 minutes. To this mixture cooled to 90° C. was added ethyl oxazoline (10 g, 100 mmol). This mixture was stirred for 10 hours at 90° C. To this mixture was added N-morpholine terminated LPEI (dp of 20) (0.53 g, 0.55 mmol, 11 mmol NH) dissolved in 20 ml of hot (90° C. toluene which had been dried by azeotropic distillation for about 15 minutes. This was immediately followed by the addition of diisopropylethylamine (12 g, 93 mmol, 8 equivalents of amine per NH). This mixture was refluxed for 48 hours. The volatiles were removed from this mixture and the resulting residue dissolved in deionized water. After ultrafiltration (MW>1000), the retentate was refluxed in 400 ml of 50% $H_2SO_4$ for 18 hours. The cooled reaction mixture was made basic to a pH$\leq$14 with KOH to produce a clear colorless liquid that floated to the top of the mixture. Upon cooling the liquid solidified. The solid was removed from the mixture and dissolved in 500 ml of hot deionized water. This mixture was allowed to cool forming a white suspension. This resulting mixture was ultracentrifuged at about 8000 rpm for about 10 minutes. The clear liquid was decanted from the white precipitate. The white precipitate was refluxed with toluene with an attached Dean-Stark trap to dry the product. The toluene mixture was evaporated of volatiles on a rotary evaporator. The remaining volatiles were removed at 0.1 mm Hg at 50° C. to give 1.8 g (70%) of the title compound. A $^{13}$C NMR spectrum of this mixture in $CDCl_3$ indicated a 65% grafting of PEOX onto LPEI as shown by integration of the terminal methyl signals versus the methylene carbon signals.

EXAMPLE 8

Preparation of a Comb-Burst PEI Wherein $N_c$ is 20, $N_b$ is 5, and G is 1.

The compound dendrimer was prepared in the same manner as in example 7 using MeOTs (3.7 g, 20 mmol), 300 ml of toluene, ethyl oxazoline, (10 g, 100 mmol), diisopropylethylamine (12 g, 93 mmol) and comb-branched PEI where $N_c$ is 20, $N_b$ is 10 and G is zero (1.0 g, 23 mmol NH maximum). Ultrafiltration, hydrolysis and drying gave 5.0 g (80% yield) of the title compound. The $^{13}$C NMR spectrum was consistent with the proposed structure.

EXAMPLE 9

Preparation of a Comb-Burst PEI Wherein $N_c$ is 20, $N_b$ is 5 and G is 2.

This example shows the use of the material formed in example 8 which was refluxed with two equivalents of PEOX having a dp of 5 per NH and 11 equivalents of diisopropylethylamine for two days. This mixture was worked up differently than the previous example. The crude PEOX-Comb-Burst PEI was hydrolyzed directly, without ultrafiltration, to give 8.6 g of a Comb-Burst and linear Polyethyleneimine (PEI). This mixture was dissolved in hot deionized water. Upon cooling the product crystallized from the mixture. The mixture was ultracentrifuged at 8000 rpm and the white precipitate was azeotropically dried with toluene to give 4.5 g for a yield of 72%.

EXAMPLE 10

Preparation of a Comb-Burst PEI Wherein $N_c$ is 20, $N_b$ is 5, and G is 3.

The preparation of Comb-Burst PEI where G is 3 incorporated improvements in the grafting step by using two equivalents of PEOX per NH and 26 mmols of diisopropylethylamine per NH. The crude material was hydrolyzed as before and the resulting mixture precipitated from PEI by making basic with KOH. Recrystallization of the cake of product floating on the KOH mixture from deionized water followed by ultracentrifugation at 8000 rpm and azeotropic drying of the white solid with toluene gave 5.6 g for a 90% yield.

EXAMPLE 11

Preparation of a Comb-Burst PEI Wherein $N_c$ is 20, $N_b$ is 5 and G is 4.

The comb-Burst PEI was prepared in a manner similar to the previous example, using two equivalents of PEOX per NH, and 23 equivalents of diisopropylethylamine per NH and refluxing two days. The crude mixture wasn't ultrafiltered but hydrolyzed with $H_2SO_4$, removed from solution by KOH and recrystallized twice from deionized water. Each recrystallization involved dissolving the product in hot water, allowing the mixture to cool to 25° C. and ultracentrifugation at 8000 rpm, 10 minutes. The clear supernatent was decanted from the white solid and the white solid was azeotropically dried with toluene. The isolated yield from the second recrystallization came to 4.9 g for a yield of 78%. The first recrystallization gave 5.5 g, for a yield of 87%.

EXAMPLE 12

Preparation of Comb-Burst PEI Wherein $N_c$ is 20, $N_b$ is 5, and G is 5.

The next generation (G) was prepared at twice the scale of all the other grafting experiments (2.0 g starting material versus 1.0 g of starting material). Only 4 to 5 equivalents of diisopropylethylamine per NH were used along with two equivalents of PEOX per NH and refluxing two days. After evaporating the volatiles the crude mixture was dissolved in deionized water and ultrafiltered using a spiral wound cartridge Amicon S1Y3 (3000 MWCO). Hydrolysis of the retentate gave an 85% yield of the title compound. The ultrafiltration with this membrane was not tried on earlier generations of G=1 to 4.

EXAMPLE 13

Preparation of Comb-Burst PEI Wherein $N_c$ is 20, $N_b$ is 5, and G is 6.

This generation was prepared in a similar manner as before using two equivalents of PEOX per NH, six equivalents of diisopropylethylamine per NH and refluxing two days. The workup again was done by ultrafiltration in deionized water using a spiral wound S1Y3 membrane. The isolated yield of PEOX-Comb-Burst after ultrafiltration came to one-half the amount normally obtained from an 80 to 90% grafting experiment. Hydrolysis of the mixture as before followed by treatment with NaOH and azeotropic drying with toluene gave only a 32% yield of the G=6 product. A repeat of this same experiment except with two recrystallizations in water instead of an ultrafiltration gave a 38% yield of the title compound.

EXAMPLE 14

Preparation of a Comb-Branched PEI Wherein $N_c$ is 20, $N_b$ is 10 and G is zero.

A mixture of MeOTs (7.4 g, 40 mmol) in 100 ml of toluene was azeotroped to dryness with a Dean-Stark trap under nitrogen for 10 to 15 minutes. To this mixture, cooled to about 90° C., was added ethyl oxazoline (39.7 g, 400 mmol). This mixture was refluxed under nitrogen for 18 hours. To this mixture was added N-morpholine terminated LPEI having a dp of 20 (1.0 g, 1.1 mmol, 23 mmol of NH) dissolved in 50 ml of hot (100° C.) toluene which had been dried by azeotropic distillation for 15 minutes. This was immediately followed by the addition of diisopropylethylamine (24 g, 186 mmol, 8 eqivalents amine per NH). This mixture was refluxed for 48 hours. The mixture was cooled, dissolved in methanol and evaporated of volatiles on a rotary evaporator and the resulting mixture was dissolved in deionized water (about 60 ml). This mixture was ultrafiltered using an Amicon spiral wound cartridge S1Y3 with the above volume as a retentate until 12 liters of permeate had been obtained (20 recirculations).This retentate was refluxed in 400 ml of 50% $H_2SO_4$ with a Dean-Stark trap collecting about 400 to 500 ml of distillate (replenishing the equivalent water) until the distillate was neutral to pH paper. This hot mixture was made basic by pouring slowly into a 50% KOH mixture under a blanket of nitrogen. The heterogenous mixture was heated to a homogeneous mixture that produces a liquid that floats to the top of the mixture. Upon cooling the liquid solidified. The solid was removed form the mixture and issolved in 500 ml of hot deionized water. This mixture was allowed to cool forming a white suspension. This resulting mixture was ultracentrifuged at 8000 rpm for about 10 minutes. The clear liquid was decanted from the white precipitate. The white precipitate was refluxed with toluene with an attached Dean-Stark trap to dry the product. The toluene mixture was evaporated of volatiles on a rotary evaporator. The remaining volatiles were removed at 0.1 mm Hg at 50° C. to give 1.8 g (70%) of the title compound. A $^{13}C$ NMR spectrum of this mixture in $CDCl_3$ indicated a 65% grafting of PEOX onto LPEI as shown by integration of the terminal methyl signals versus the methylene carbon signals.

EXAMPLE 15

Preparation of a Comb-Branched PEI Wherein $N_c$ is 20, $N_b$ is 10 and G is Zero.

A mixture of morpholine-terminated LPEI having a dp of 20 (1.04 g, 22 mmol), PEOX oligomers having a dp of 10 (47.5 g, 40 mmol) and diisopropylethylamine (20 g, 6 to 7 equivalents per NH) were refluxed under nitrogen obtained from a nitrogen cylinder (constant pressure and no flow) and a Hg bubbler for 48 hours. The volatiles were removed from the mixture and the resulting yellow orange residue was dissolved in 1 liter of deionized water. The mixture was ultrafiltered with an Amicon spiral wound cartride using 700 ml of retentate and 8.5 liters of permeate to give 24 grams of the PEOX-Comb-Branched PEI copolymer. The material was hydrolyzed with 50% $H_2SO_4$ and the resulting mixture added to an excess of 50% KOH. The cake floating on the KOH was mixed with toluene and azeotropically dried under nitrogen to give 10.1 g (90%) of the Comb-branched PEI dendrimer.

EXAMPLE 16

Preparation of a Comb-Burst PEI Wherein $N_c$ is 20, $N_b$ is 10 and G is One.

The preparation of G=1 of this Comb-Burst PEI series was identical in all respects to the preparation of G=0. The isolated yield of the title compound from 1.1 g of G=0 Comb-branched PEI was 10.5 g (84%). The $^{13}C$ NMR system showed a little more of the carbinol signal at 60.1 ppm than before, plus a signal at 59.46 ppm.

EXAMPLE 17

Preparation of Comb-burst PEI Wherein $N_c$ is 20, $N_b$ is 10 and G is 2.

This material was prepared as described in the previous preparations utilizing an Amicon S1Y10 sprial wound ultra-filtration cartridge (10,000 MWCO) (600 ml retentate/9 liters of permeate). From 1.1 g of Comb-burst PEI wherein G=1, there was obtained 10.8 g (86%) of the title product. The $^{13}C$ NMR spectrum indicated more of the signal at 60.1 ppm than at 59.67 ppm.

EXAMPLE 18

Preparation of a Comb-burst PEI Wherein $N_c$ is 20, $N_b$ is 10 and G is 3.

The material was prepared as described before using an Amicon S1Y10 sprial wound ultrafiltration cartridge (10,000 MWCO) and filtration volumes as described before. From 1.1 g (25 mmol NH) of Comb-burst PEI dendrimer wherein $N_c$ is 20, $N_b$ is 10 and G is 2 there was obtained 10.3 g (82%) of the Comb-burst PEI dendrimer wherein $N_c$ is 20, $N_b$ is 10, and G is 3. The $^{13}C$ NMR spectrum of the material again indicated carbinol signals at 60.1 ppm and 57 ppm.

EXAMPLE 19

Preparation of Comb-burst PEI Wherein $N_c$ is 20, $N_b$ is 10 and G is 4.

This material was prepared as described above using an Amicon S1Y10 spiral wound ultrafiltration cartridge with the volumes indicated above. From 1.1 g (25 mmol NH maximum) of Comb-burst PEI dendrimer wherein $N_c$ is 20, $N_b$ was 10, and G was 3, there was obtained 10.1 g of the title compound. (80% yield).

EXAMPLE 20

Preparation of a Comb-burst PEI Wherein $N_c$ is 20, $N_b$ is 10, and G is 5.

This material was prepared as described above utilizing 1.1 g (25.5 mmol NH) of Comb-burst PEI wherein $N_c$ is 20, $N_b$ is 10 and G is 4, 47.5 g (40 mmol) of PEOX oligomer, and 25 g (8 equivalents of amine per NH) of diisopropyl-ethylamine. Workup as before using an Amicon S1Y10 spiral wound cartridge (700 ml of retentate, and 9 liters of permeate) gave 18 g of the PEOX-Comb-burst copolymer. Hydrolysis with 50% $H_2SO_4$ and treatment with excess NaOH gave a cake of material that floated on the caustic mixture with a lot of trapped NaOH and sodium sulfate salts. The cake was heated in 300 ml of deionized water to boiling and allowed to cool giving a white precipitate. This mixture was ultracentrifuged at 8000 rpm for 10 minutes and the resulting clear liquid was poured from the settled white solid. This white solid was mixed with toluene and dried by azeotropic distillation to give 7.0 g (56%) of the title compound.

EXAMPLE 21

Preparation of a Comb-branched PEI Wherein $N_c$ is 20, $N_b$ is 20 and G is Zero.

A PEOX oligomer having a dp of 20 was prepared from MeOTs (7.5 g, 40 mmol) and ethyl oxazoline 80 g, 800 mmol) by refluxing under tank nitrogen using a Hg bubbler. The LPEI (0.5 g, 0.52 mmol, 10 mmol per NH) in hot toluene was added to the PEOX oligomer followed by diisopropylethylamine (74 g, 574 mmol, 29 mmol per NH). This mixture was refluxed for 72 hours. The volatiles were removed and the resulting residue was dissolved in deionized water. This mixture was ultrafiltered using a S1Y3 cartridge. Workup as before gave 9.8 g of a PEI product (theory 9.1 g). The $^{13}C$ NMR spectrum of this material indicated a significant amount of a carbinol signal at 60.2 ppm.

EXAMPLE 22

Preparation of a Comb-Branched PEI polymer Wherein $N_c$ is 20, $N_b$ is 20 and G is Zero In this experiment, two equivalents of PEOX oligomer per NH of the PEI and diisopropylethylamine (30 equivalents per NH of PEI) were refluxed for five days. A very large stir bar was used to get more efficient stirring of the mixture than was obtained in the above experiment. The mixture was stripped of volatiles and the resulting residue dissolved in deionized water. Ultrafiltration of this mixture using the S1Y3 spiral wound cartiride gave no separationas as determined by SEC. The SEC plot indicated two peaks. Upon co-injection with authentic PEOX oligomer having a dp of 20, one of the peaks was enhanced. The ultrafiltration was then carried out on a S1Y10 (10,000 MWCO) spiral wound cartridge. The SEC plot of the retentate was identical to the S1Y3 cartridge retentate.

The ultrafiltration was switched to an Amicon flat stock stirred cell system using a YM10 (10,000 MWCO) cartridge. After 1.5 liters of permeate only a small amount of the presumed PEOX oligomer having a dp of 20 had been ultrafiltered.

The material was then ultrafiltered with the flat stock stirred cell using a YM 30 membrane (30,000 MWCO) (100 ml, retentate; 2000 ml permeate) to give a good separation by SEC. The retentate evaporated to 18 g (42%) of the PEOX-Comb-branched PEI copolymer. This material hydrolyzed to 7.0 g (38%) of the Comb-branched PEI. The $^{13}C$ NMR spectrum of the Comb-branched PEI indicated only a minor amount (about 10%) of the carbinol signal at 60.1 ppm relative to the methyl terminated signal at 36.5 ppm.

EXAMPLE 23

Preparation of a Comb-Burst PEI Polymer Wherein $N_c$ is 20, $N_b$ is 20 and G is One.

This material was prepared with two equivalents of PEOX oligomer having a dp of 20 and refluxing with diisopropylethylamine for three days. The reaction parameters were to be held constant to permit a reasonable analysis of the chemistry. An analysis of the crude reaction mixture by SEC at 48 hours, 72 hours and 96 hours indicated a progressive increase in molecular weight. Ultrafiltration of the crude material in water with the Amicon flat stock stirred cell using a YM30 (30,000 MWCO) membrane as before (100 ml, retentate; 2000 ml permeate) gave a 74% yield of the PEOX-Comb-burst PEI copolymer. Hydrolysis and treatment with NaOH, recrystallization from water, and azeotropic drying in toluene, gave a 68% yield of the title compound.

EXAMPLE 24

Preparation of a Comb-Branched Phi Polymer Wherein $N_c$ is 20, $N_b$ is 100 and G is Zero.

Further exploration of the PEOX chain length on the grafting efficiency was done. A PEOX having a dp of 100 was prepared (24 hrs at reflux) and refluxed 65 hours with PEI (1 equivalent PEOX per NH) with 11 equivalents of diisopropylethylamine per NH. The mixture was evaporated of volatiles, dissolved in deionized water and ultrafiltered with an S1Y30 (30,000 MWCO) cartridge. Hydrolysis of the retentate and workup gave a 31% yield of a white amorphous powder. Hydrolysis of the permeate gave a white crystalline material, LPEI having a dp of 100.

EXAMPLE 25

Preparation of a Styrene Core Polymer

The styrene core polymer precursor was prepared by polymerization of 20 g (192 mmol) of styrene in benzene (20 ml), initiated by s-butyl lithium (4 mmol). After 4 hours, the reaction was terminated by addition of methanol (1 ml.) Chloromethylation of the product polymer (10 g polystyrene, 60 ml chloromethyl methyl ether, and 1 ml stannic chloride in 500 ml of carbon tetrachloride for 48 hours) gave the chloromethylated core polymer.

EXAMPLE 26

Preparation of a Comb-Branched Polystyrene Wherein G is Zero.

Living polystyrene oligomer was generated by initiation of 20 g of styrene by 4 mmol of s-butyl lithium, as in example 25. After 4 hours at room temperqture, 6 mmol of diphenylethylene in 350 ml of tetrahydrofuran was added. The chloromethylated polystyrene core was added portionwise, over 30 minutes, until most of the orange color of the carbanion had disappeared. After an additional 30 minutes, residual carbanions were terminated by the addition of 1 ml of methanol. Evaporation of the solvent and fractionation in toluene/methanol gave an 80% yield of the title compound.

EXAMPLE 27

Preparation of a Comb-Burst Polystyrene Polymer Wherein G is Equal to One.

The product of example 26 was chloromethylated as described in example 25. Grafting was carried out as described in example 26, substituting the chloromethylated-comb-branched material for the linear-chloromethylated-polystyrene core.

EXAMPLE 28

Preparation of a Comb-Burst Polystyrene Polymer Wherein G is 2.

The product of example 27 was chloromethylated as described in example 25. Grafting was carried out as described in example 26, substituting the chloromethylated-comb-burst material for the linear-chloromethylated-polystyrene core.

EXAMPLE 29

Preparation of Rod-Shaped Comb-Burst PEI wherein $N_c$ is 200, $N_b$ is 5 and G is 3.

This material was prepared as described above using N-morpholine terminated PEI as an initiator core. Repeated grafting (4 times) with Methyl Tosylate (3.7 g, 20 mmol) and ethyl oxazoline (10 g, 100 mmol) in 100 ml of toluene, followed by hydrolysis with 150 ml of 50% $H_2SO_4$ gave the dendrimers in a 70 to 80% yields. These products were characterized by $^{13}$C-NMR spectroscopy, titration and electrophoresis and shown to be the titled material.

EXAMPLE 30

Preparation of Spherically-Shaped Comb-Burst PEI wherein $N_c$ is 10, $N_b$ is 100 and G is 3.

This material was prepared in the same manner as the rod-shaped dendrimer using LPEI (dp of 10) as an initiator core. The branches were constructed with PEOX (dp of 100), initiated as shown in the examples above.

EXAMPLE 31

Synthesis of Ring Core Hyper-Combbranched Polymers

AZACROWN™ (1,4,7,10-tetraazacyclododecane, cyclen) was obtained from The Dow Chemical Company, and was further recrystallized from toluene. The purified AZACROWN™ is a white needle-like crystal.

A mixture of methyl tosylate (MeOTs)(0.922 g, 4.95 mmol) in 100 ml of toluene was azeotroped to remove water with a distillation head under Ar for 10 minutes. After cooling to ~90° C., 2-ethyloxazoline (10 ml, 99.06 mmol) was cannulated in and the mixture was allowed to reflux for 5 hours. To this mixture was added a AZACROWN™ core (0.214 g, 4.95 mmol of NH), which was dried by azeotropic distillation from toluene, followed by immediate addition of diisopropylethylamine (i-Pr$_2$NEt)(2–4 eq.). The mixture was refluxed for 1 hour, cooled, and then dissolved in methanol (~100% grafting yield as determined by SEC). After rotary-evaporation of the solvents, the crude product was either purified by ultrafiltration with Amicon spiral wound cartridges S1Y3 (3,000 MWCO), or fractionated by methanol/diethyl ether mixture to remove the unreacted monomers, oligomers, and catalysts. The entire separation process was monitored by size exclusion chromatography (SEC). The purified product was rotary-evaporated and lyophilized to give a ring-branched polyethyloxazoline-polyethyleneimine (PEOX-PEI) polymer as a white powder. The higher generations of the ring core combburst polymers can be prepared in a similar manner as described in the linear core case as described above. All the products were analyzed by size exclusion chromatography (SEC), capillary electrophoresis (CE), nuclear magnetic resonance (NMR), and electrospray mass spectroscopy (ES-MS).

EXAMPLE 32

Synthesis of Hyper-Terminally Branched Core Hyper-Comb-branched Polymers

A mixture of MeOTs (0.39 g, 1.98 mmol) in 100 ml of toluene was azeotroped to remove water with a distillation head under Ar for 10 minutes. After cooling to ~90° C., 2-ethyloxazoline (10 ml, 99.06 mmol) was cannulated in and the mixture was allowed to reflux for 5 hours. To this mixture was added a hyper-branched polyethylene amine core (0.214 g, 4.95 mmol of NH), which was dried by azeotropic distillation from toluene, followed by immediate addition of i-$Pr_2$NEt (large excess). The mixture was refluxed for 3 hours, cooled, and the top toluene solution was decanted off. The remaining viscous oil was redissolved in a small amount of MeOH and reprecipitated out in diethyl ether ($Et_2O$). After the top $Et_2O$ solution was decanted, the bottom precipitate was redissolved in methanol (MeOH) and dried over rotary evaporator and high vacuum to give a light yellow polyethyloxazoline-polyethyleneamine (PEOX-PEA) polymer. The higher generations of the hyper-branched core combburst polymers can be prepared in a similar manner as described in the linear core case described above. All the products were analyzed by SEC and NMR. Instrumental for Examples 31 and 32.

SEC measurements were performed on a series of Beckman TSK 4000 PW (or POLY-OH, Polymer Laboratory), 3000 PW, and 2000 PW columns using Waters 510 HPLC pump, Thermo Separation Products AS 3000 Autosampler, Wyatt DAWN DSP-F Multi Angle Laser Light Scattering Detector, and Wyatt interferometer refractometer (Optilab 903). $^1$H and $^{13}$C NMR spectra were obtained on Brucker 360 MHz or Varian Unity 300 MHz NMR spectrometer using either $CDCl_3$ or MeOD as solvents. Purity of monomers was checked by GC (HP 5890, He as carrier gas). Ultra filtration was achieved using either an Amicon 3,000 or 10,000 molecular weight cut off (MWCO) membrane. CE was performed on Beckman P/ACE System 2050 (Software System Gold). The polymer MWs were also measured by ES-MS (Finnigan Mat TSQ 700).

EXAMPLE 33

Preparation of Poly (2-Ethyloxazoline) and Polyethyleneimine Linear Polymers (DP=10, 20, 50, 100, and 200).

Methyl p-toluenesulfonate, 2-ethyloxazoline, morpholine and diisopropyl ethylamine were purchased from Aldrich. Methyl p-toluenesulfonate was purified by distillation, while 2-ethyloxazoline, morpholine, diisopropyl ethylamine and toluene were stirred over $CaH_2$ and distilled prior to use. All the reactions were performed under an ultra pure Ar atmosphere.

The synthesis of poly(2-ethyloxazoline), (PEOX20, DP=20) is described to illustrate the general procedure for the preparation of linear PEOX. To a 250 ml two-neck round bottom flask was added methyl p-toluenesulfonate (7.45 g, 40 mmol) and dry toluene (150 ml). A distillation head (vacuum type) was attached and trace amounts of water in the mixture were removed by azeotroping with toluene for 10–15 minutes. After cooling to about 90° C., ethyloxazoline (80.8 ml, 800 mmol) was cannulated in, and the mixture was allowed to reflux for 10 hours before termination with excess morpholine. During the polymerization, a cloudy PEOX suspension was formed. After the termination with morpholine, the solution become clear again. The crude mixture was rotary-evaporated and then hydrolyzed with 500 ml of 50% $H_2SO_4$, followed by azeotroping the water-propionic acid mixture with a Dean Stark trap until the pH of the distillate was neutral. This hot acidic solution was slowly added (with a separatory funnel) into a 50% NaOH solution cooled by an ice bath. This solution (pH $\geq$11) was heated to boil under $N_2$, and the product (linear PEI) floated on top as an oily layer. After cooling to room temperature, the top layer became a solid cake on the surface which was subsequently removed and redissolved in 600 ml deionized, boiling water. After slow sedimentation overnight, the white precipitate was filtered by suction funnel.

In order to completely remove excess NaOH, cold water was used to exhaustively wash the precipitate until pH of the flitrate solution was neutral. Pure polymer was obtained by azeotropic removal of water from a toluene solution of the polymer, followed by a gravity filtration and then rotary evaporating the toluene at 60° C. Such polymer was further dried under high vacuum overnight (33 g., 85.8% yield, MW=1,130, MWD=1.05). Linear PEOX and PEI 10, 50, 100, and 200 were prepared in a similar manner (PEOX yield $\geq$90%, PEI yield $\geq$80%). All the polymers were analyzed by SEC, ES-MS, NMR, CE, and PAGE.

EXAMPLE 34

Synthesis of Comb-branched Polymers (GO).

The synthesis of PEOX10-g-PEI20 is provided as a general procedure for the preparation of Comb-branched PEOX-PEI and PEI polymers. A mixture of MeOTs (7.38 g, 39.62 mmol) in 150 ml of toluene was azeotroped to remove water with a distillation head under Ar for 10 minutes. After cooling to about 90° C., 2-ethyloxazoline (40 ml, 396.24 mmol) was cannulated in and the mixture was allowed to reflux for 5 hours. To this mixture was added morpholine terminated LPEI 20 (1.90 g, 39.62 mmol of NH), which was dried by azeotropic distillation from toluene, followed by immediate addition of i-$Pr_2$NEt (1 to 2 eq.). The mixture was refluxed for 1 hour, cooled, and then dissolved in methanol (about 75% grafting yield as determined by SEC). After rotary-evaporation of the solvents, the crude product was either purified by ultrafiltration with Amicon spiral wound cartridges S1Y3 (3,000 MWCO), or fractionated by methanol/diethyl ether mixture to remove the unreacted monomers, oligomers, and catalysts. The entire separation process was monitored by SEC. The purified product was rotary-evaporated and lyoplilized to give a comb-branched PEOX-PEI polymers as a white powder. This white powder was further hydrolyzed in 50% $H_2SO_4$ at 100° C. and purified as described before to provide a PEI comb-branched polymer as a white viscous oil (MW=2,500, MWD=1.22). Comb-branched PEOX20-g-PEI20, PEOX10-g-PEI50, PEOX50-g-PEI20, PEOX100-g-PEI50, PEOX200-g-PEI50, and PEOX20-g -1,4,7,10-Tetraazacylododecane) (PEOX20-g-Azacrown) were also prepared in a similar manner. All the products were analyzed by SEC-multi angle laser light scattering, CE, NMR, ES-MS and PAGE.

EXAMPLE 35

Synthesis of Comb-branched Polymers (G1).

A mixture of MeOTs (0.738 g, 3.962 mmol) in 150 ml of toluene was azeotroped to dryness with a distillation head under Ar for 10 minutes. After cooling to about 90° C., 2-ethyloxazoline (40 ml, 396.24 mmol) was cannulated in and the mixture was allowed to reflux for 10 hours. To this mixture was added Comb-branched PEI (0.209 g, about 3.962 mmol of NH) dried by azeotropic distillation from toluene, followed by immediate addition of i-Pr$_2$NEt (1–2 eq.). The mixture was refluxed for 1 hour, and then cooled to room temperature. The top toluene solution was decanted off and the bottom polymer product was redissolved in methanol. This crude product was purified by refractionation with a methanol/diethyl ether mixture to remove the unreacted monomers, oligomers, and catalysts. The entire separation was monitored by SEC. The purified product was rotary-evaporated and lyophilized to give the Comb-branched PEOX-PEI polymer as a white powder (MW=260,000, MWD=1.10). The grafting yield depends on the length of the side chains (normally around 40%–80% as determined by SEC). Shorter side chains give a higher grafting yield. This white powder was further hydrolyzed in 50% H$_2$SO$_4$ at 100° C. and purified as described before to provide a PEI Comb-branched polymer as a white solid (80% yield, MW=138,800, MWD=1.34).

EXAMPLE 36

Synthesis of Comb-branched (G2).

A mixture of MeOTs (0.738 g, 3.962 mmol) in 150 ml of toluene was azeotroped to dryness with a distillation head under Ar for 10 minutes. After cooling to about 90° C., 2-ethyloxazoline (40 ml, 396.24 mmol) was cannulated in and the mixture was allowed to reflux for 10 hours. To this mixture was added Comb-branched PEI polymer (0.200 g, about 3.962 mmol of NH) dried by azeotropic distillation from toluene, followed by immediate addition of i-Pr$_2$NEt (1–2 eq.). The mixture was refluxed for 1 hour, and then cooled to room temperature. The top toluene solution was decanted off and the bottom polymer product was redissolved in methanol. This crude product was purified by refractionation with a methanol/diethyl ether mixture to remove the unreacted monomers, oligomers, and catalysts. The entire separation was monitored by SEC. The purified product was rotary-evaporated and lyophilized to give the Comb-branched PEOX-PEI polymer as a white powder (MW=2,182,000, MWD=1.50). This white powder was further hydrolyzed in 50% H$_2$SO$_4$ at 100° C. and purified as described before to provide PEI Comb-branched polymers as a white solid (85% yield, MW=1,078,000, MWD=1.47). All the products were analyzed by SEC, CE, NMR and PAGE, viscometry, TGA, and DSC.

EXAMPLE 37

Synthesis of Comb-branched (G3)

The G3 Comb-branched polymer was synthesized in a similar manner as above. The molecular weight of the resulting product was 10,400,000 and the molecular weight distribution was 1.20. The higher generation Comb-branched polymers and other Comb-branched polymers with different shapes due to the different side chains and initiator cores used were prepared in a similar manner. Instrumental For Examples 33–37

SEC measurements were perforated on a series of Beckman TSK 4000 PW (or POLY-OH, Polymer Laboratory), 3000 PW, and 2000 PW columns using Waters 510 HPLC pump, Thermo Separation Products AS 3000 Autosampler, Wyatt DAWN DSP-F Multi Angle Laser Light Scattering Detector, and Wyatt interferometer refractometer (Optilab 903). $^1$H and $^{13}$C NMR spectra were obtained on Brucker 360 MHz or Varian Unity 300 MHz NMR spectrometer using either CDCl$_3$ or MeOD as solvents. Purity of monomers was checked by GC (HP 5890, He as carrier gas). Ultrafiltration was achieved using an Amicon 3,000, 10,000, or 100,000 molecular weight cut off (MWCO) membrane. Thermal analysis was performed on DuPont Thermal Gravimetric Analyzer (Model 951) with TA Instrumental Software (2000 Series). CE was performed on Beckman P/ACE System 2050 (Software System Gold). The polymer MWs were also measured by ES-MS (Finnigan Mat TSQ 700). PAGE analysis was performed on Gradipore gradient microgel (5–40% T) with a BioRad. 500/200 power supply. The viscosity measurements were achieved on a Cannon-Ubbelohde semi-micro viscometer.

What is claimed is:

1. A process for producing non-crosslinked poly-branched polymers having the general formula

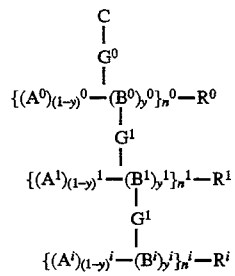

wherein: C is a core molecule; each {(A)-(B)} branch is a linear polymer or copolymer chain; each R is the residual moiety of an initiator;

A and B are polymerizable monomers or comonomers capable of withstanding the conditions required for branching therefrom or grafting thereto, at least during the polymerization of the {(A)-(B)} linear polymer chain and during its grafting to a prior {(A)-(B)} branch; each G is a grafting component, and the designation

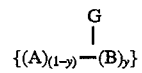

indicates that G can extend from either an (A) unit or a (B) unit;

n is the degree of polymerization of the indicated generation comb branches, y is the fraction of B units in the indicated generation branch, and has a value of 0.01 to 1;

the superscripts 0, 1 and i designate the comb-branch generation level, with i beginning at "2" and continuing for the number of reiterative branch set generations in the polymer; and at least n$^0$ and n$^1$ are $\geq 2$;

said process comprising (I) forming a core having at least one reactive site;

(II) reacting essentially all of the reactive sites of said core with a reactive polymer having the unit formula

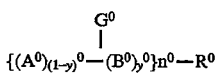

to form multiple branches which contain reactive ($B^0$) sites on each branch, using a reactive scheme such that the reactive monomer units ($B^0$) are capable of withstanding the conditions required for branching therefrom or grafting thereto to ensure that said reactive polymer

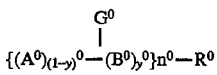

reacts with said reactive sites of said core, but that no reactions occur at said ($B^0$) sites;

(III) repeating step (II) sequentially by reacting reactive polymer having the unit formula

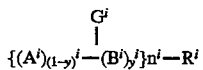

with the reactive sites of said polymerizable $B^{(i-1)}$ monomers or comonomers of the previous generation to form successive generation of branches to give the desired non-crosslinked poly-branched polymer.

2. The process of claim 1 in which linear polyethylene amine is used as said initiator core and oxazoline based oligomers are grafted thereto to form zero generation branches having nonreactive oxazoline groups thereon, said zero generation branches then being hydrolyzed to form reactive amine sites to which first generation oxazoline oligomers are then grafted, said hydrolysis and subsequent reaction steps being then sequentially reiterated to form the desired non-crosslinked poly-branched polymer.

3. A process as claimed in claim 2 wherein the oxazoline oligomer is poly-2-alkyl substituted oxazoline.

4. A process as claimed in claim 3 wherein the oxazoline oligomer is poly-2-aryl substituted oxazoline.

5. A process for producing a poly-branched polymer having a relatively high molecular weight in a relatively low number of iterations, said process comprising:
(a) forming a first set of branches by initiating polymerization of a first set of monomers which are either protected against or non-reactive to branching and grafting during said polymerization, wherein each of said branches has (i) a reactive end unit upon completion of said polymerization, and (ii) said reactive end units being incapable of reacting with each other;
(b) grafting said branches to a core having a plurality of core reactive sites capable of reacting with said reactive end units of said branches;
(c) either deprotecting or activating a plurality of monomeric units on each of said branches to create branch reactive sites;
(d) forming a second set of branches by repeating step (a) above with a second set of monomers;
(e) attaching said second set of branches to said first set of branches by reacting said reactive end units of said second set of branches with said branch reactive sites on said first set of branches, and thereby form said poly-branched polymer; and
(f) repeating steps (c), (d), and (e) reiteratively to form subsequent sets of branches and attach them to the preceding set of branches, until a desired number of iterations has been effected.

6. The product of claim 5 produced in 3 repetitions of steps (c), (d), and (e), and having a molecular weight of from about 1 million to about 10 million.

7. The product of claim 5 produced in 4 repetitions of steps (c), (d), and (e), and having a molecular weight of from about 10 million to about 50 million.

8. The process of claim 5 wherein the use of NaOH is avoided during said process.

9. The process of claim 5 further comprising:
(g) separating said high molecular weight poly-branched polymer from a reaction mixture.

10. The process of claim 8 wherein said poly-branched polymer is dried at temperatures less than about 60° C.

11. The process of claim 9 wherein said poly-branched polymer is maintained at a temperature of about 20° C.

12. A process for producing a poly-branched polymer having a relatively high molecular weight in a relatively low number of iterations, said process comprising:
(a) forming a first set of branches by initiating polymerization of a first set of monomers which are either protected against or non-reactive to branching and grafting during said polymerization, wherein each of said branches has (i) a degree of polymerization of at least about 50, (ii) a reactive end unit upon completion of said polymerization, and (iii) said reactive end units being incapable of reacting with each other;
(b) grafting said branches to a core having a plurality of core reactive sites capable of reacting with said reactive end units of said branches;
(c) either deprotecting or activating a plurality of monomeric units on each of said branches to create branch reactive sites;
(d) forming a second set of branches by repeating step (a) above with a second set of monomers; and
(e) attaching said second set of branches to said first set of branches by reacting said reactive end units of said second set of branches with said branch reactive sites on said first set of branches, and thereby form said poly-branched polymer.

13. The process of claim 12 wherein at least one of said first set and said second set of branches have a degree of polymerization of at least about 100.

14. The process of claim 12 wherein said grafting step is performed utilizing a grafting ratio of from about 0.8 to about 1.2 reactive end units per core reactive sites, and in the presence of a proton scavenger, said proton scavenger being present in a ratio of at least about 1 equivalent of proton scavenger for every reactive end unit of said first set and said second set of branches.

15. The process of claim 14 wherein said proton scavenger is a suitable base that is compatible with said polymeric core and said first set and said second set of branches.

16. The process of claim 15 wherein said proton scavenger is a base selected from the group consisting of i-$Pr_2$NEt, triisobutylamine, triisooctylamine, triethylamine, and combinations thereof.

17. The process of claim 12 wherein said grafting step is performed for a time period of less than about 1 hour.

18. The process of claim 12 wherein said forming said first set of branches is performed for a time period of less than about 5 hours.

19. The process of claim 12 wherein said forming said second set of branches is performed for a time period of less than about 10 hours.

20. The process of claim 12 further comprising:
(f) ensuring that NaOH or other salts are removed from at least one of said first set of branches, said second set of branches, and said poly-branched polymer.

21. The process of claim 12 further comprising:
(f) separating said high molecular weight poly-branched polymer from a reaction mixture.

22. The process of claim 21 wherein said poly-branched polymer is PEI hyper-comb-branched polymer and said polymer is dried at temperatures less than about 60° C.

23. The process of claim 22 wherein said poly-branched polymer is maintained at a temperature of about 20° C.

24. The process of claim 21 wherein said separating step is performed by a polymer refractionation technique comprising:
(i) forming a first mixture comprising said high molecular weight poly-branched polymer and unwanted lower molecular weight components;
(ii) adding an alcohol solvent to said mixture such that said poly-branched polymer and said lower molecular weight components are dissolved; and
(iii) incrementally adding a poor solvent thereby causing said high molecular weight products to form a precipitate, until substantially all of said poly-branched polymer is in said precipitate.

25. The process of claim 24 wherein said alcohol solvent is methanol.

26. The process of claim 24 wherein said poor solvent is diethyl ether or hexane.

27. The product produced by the process of claim 12.

28. The process of claim 12 wherein steps (c), (d), and (e) are reiteratively repeated to form subsequent sets of branches and attach each set of branches to the preceding set of branches until a desired number of iterations has been effected.

29. The product produced by the process of claim 28.

30. The product of claim 29 produced in 3 repetitions of steps (c), (d), and (e), and having a molecular weight of from about 1 million to about 10 million.

31. The product of claim 29 produced in 4 repetitions of steps (c), (d), and (e), and having a molecular weight of from about 10 million to about 50 million.

32. A process for producing a poly-branched polymer having a relatively high molecular weight in a relatively lower number of iterations, said process comprising:
(a) forming a first set of branches by initiating polymerization of a first set of monomers which are either protected against or non-reactive to branching and grafting during said polymerization, wherein each of said branches has (i) a reactive end unit upon completion of said polymerization, and (ii) said reactive end units being incapable of reacting with each other;
(b) grafting said branches to a core having a plurality of core reactive sites capable of reacting with said reactive end units of said branches, wherein said grafting is performed utilizing a grafting ratio of from about 0.8 to about 1.2 reactive end units per core reactive sites;
(c) either deprotecting or activating a plurality of monomeric units on each of said branches to create branch reactive sites;
(d) forming a second set of branches by repeating step (a) above with a second set of monomers; and
(e) attaching said second set of branches to said first set of branches by reacting said reactive end units of said second set of branches with said reactive sites on said first set of branches, and thereby form said poly-branched polymer.

33. The process of claim 32 wherein said grafting operation is performed utilizing a grafting ratio of about 1 reactive end unit per 1 core reactive site.

34. The process of claim 32 wherein said grafting operation is performed in the presence of a proton scavenger, said proton scavenger being in a concentration of at least 1 equivalent of proton scavenger per said reactive end unit of said first set of branches.

35. The process of claim 34 wherein said proton scavenger is a base selected from the group consisting of i-Pr$_2$NEt, triisobutylamine, triisooctylamine, and triethylamine, and combinations thereof.

36. The process of claim 32 wherein said grafting step is performed for a time period of less than about 1 hour.

37. The process of claim 32 wherein said forming at least one of said first set and said second set of branches is performed for a time period of less than about 5 hours.

38. The process of claim 32 further comprising:
(f) ensuring that NaOH or other salts are removed from at least one of said first set of branches, said second set of branches, and said poly-branched polymer.

39. The process of claim 32 further comprising:
(f) separating said high molecular weight poly-branched polymer from a reaction mixture.

40. The process of claim 39 wherein said poly-branched polymer is PEI hyper-comb-branched polymer and said polymer is dried at temperatures less than about 60° C.

41. The process of claim 40 wherein said poly-branched polymer is maintained at a temperature of about 20° C.

42. The process of claim 39 wherein said separating step is performed by a polymer refractionation technique comprising:
(i) forming a first mixture comprising said high molecular weight poly-branched polymer and unwanted lower molecular weight components;
(ii) adding an alcohol solvent to said mixture such that said poly-branched polymer and said lower molecular weight components are dissolved; and
(iii) incrementally adding a poor solvent thereby causing said high molecular weight products to form a precipitate, until substantially all of said poly-branched polymer is in said precipitate.

43. The process of claim 42 wherein said alcohol solvent is methanol.

44. The process of claim 42 wherein said poor solvent is at least one of diethyl ether and hexane.

45. The product produced by the process of claim 32.

46. The process of claim 32 wherein steps (c), (d), and (e) are reiteratively repeated to form subsequent sets of branches and attach each set of branches to the preceding set of branches until a desired number of iterations has been effected.

47. The product produced by the process of claim 46.

48. The product of claim 47 produced in 3 repetitions of steps (c), (d), and (e), and having a molecular weight of from about 1 million to about 10 million.

49. The product of claim 47 produced in 4 repetitions of steps (c), (d), and (e), and having a molecular weight of from about 10 million to about 50 million.

50. A process for producing a poly-branched polymer having a relatively high molecular weight in a relatively low number of iterations, said process comprising:
(a) forming a first set of branches by initiating polymerization of a first set of monomers which are either protected against or non-reactive to branching and grafting during said polymerization, wherein each of said branches has (i) a reactive end unit upon completion of said polymerization, and (ii) said reactive end units being incapable of reacting with each other;

(b) grafting said branches to a core having a plurality of core reactive sites capable of reacting with said reacting end units of said branches, wherein said grafting step is performed in a time period of less than about 1 hour;

(c) either deprotecting or activating a plurality of monomeric units on each of said branches to create branch reactive sites;

(d) forming a second set of branches by repeating step (a) above with a second set of monomers; and (e) attaching said second set of branches to said first set of branches by reacting said reactive end units of said second set of branches with said branch reactive sites on said first set of branches, and thereby form said poly-branched polymer.

51. The process of claim 50 further comprising:

(f) ensuring that NaOH or other salts are removed from at least one of said first set of branches, said second set of branches, and said poly-branched polymer.

52. The process of claim 50 further comprising:

(f) separating said high molecular weight poly-branched polymer from a reaction mixture.

53. The process of claim 52 wherein said poly-branched polymer is PEI hyper-comb-branched polymer and said polymer is dried at temperatures less than about 60° C.

54. The process of claim 53 wherein said poly-branched polymer is maintained at a temperature of about 20° C.

55. The process of claim 52 wherein said separating step is performed by a polymer refractionation technique comprising:

(i) forming a first mixture comprising said high molecular weight poly-branched polymer and unwanted lower molecular weight components;

(ii) adding an alcohol solvent to said mixture such that said poly-branched polymer and said lower molecular weight components are dissolved; and (iii) incrementally adding a poor solvent thereby causing said high molecular weight products to form a precipitate, until substantially all of said poly-branched polymer is in said precipitate.

56. The product produced by the process of claim 50.

57. The process of claim 50 wherein steps (c), (d), and (e) are reiteratively repeated to form subsequent sets of branches and attach each set of branches to the preceding set of branches until a desired number of iterations has been effected.

58. The product produced by the process of claim 57.

59. The product of claim 58 produced in 3 repetitions of steps (c), (d), and (e), and having a molecular weight of from about 1 million to about 10 million.

60. The product of claim 58 produced in 4 repetitions of steps (c), (d), and (e), and having a molecular weight of from about 10 million to about 50 million.

61. A process for producing a poly-branched polymer having a relatively high molecular weight in a relatively low number of iterations, said process comprising:

(a) forming a first set of branches by initiating polymerization of a first set of monomers which are either protected against or non-reactive to branching and grafting during said polymerization, wherein each of said branches has (i) a degree of polymerization of at least about 50, (ii) a reactive end unit upon completion of said polymerization, and (iii) said reactive end units being incapable of reacting with each other;

(b) grafting said branches to a core having a plurality of core reactive sites capable of reacting with said reacting end units of said branches, wherein said grafting step is performed utilizing a grafting ratio of from about 0.8 to about 1.2 reactive end units per core reactive sites, and wherein said grafting step is also performed in the presence of a proton scavenger, said scavenger being present in a concentration of at least about 1 equivalent of scavenger for every reactive end unit, and wherein said grafting step is performed in a time period of less than about 1 hour;

(c) either deprotecting or activating a plurality of monomeric units on each of said branches to create branch reactive sites;

(d) forming a second set of branches by repeating step (a) above with a second set of monomers;

(e) attaching said second set of branches to said first set of branches by reacting said reactive end units of said second set of branches with said branch reactive sites on said first set of branches, and thereby form said poly-branched polymer; and (f) performing at least one of the following steps: (i) ensuring that NaOH or other salts are removed from at least one of said first set of branches, said second set of branches, and said poly-branched polymer, and (ii) ensuring that said poly-branched polymer is dried at temperatures less than about 60° C.

62. The process of claim 61 further comprising:

(g) forming a mixture comprising said poly-branched polymer and unwanted lower molecular weight components;

(h) adding an alcohol solvent to said mixture such that said poly-branched polymer and said lower molecular weight products are dissolved; and (i) incrementally adding a poor solvent thereby causing said high molecular weight product to form a precipitate, until substantially all of said poly-branched polymer is in said precipitate.

63. The process of claim 61 wherein steps (c), (d), and (e) are reiteratively repeated to form subsequent sets of branches and attach each set of branches to the preceding set of branches until a desired number of iterations has been effected.

64. The product produced by the process of claim 63.

65. The product of claim 64 produced in 3 repetitions of steps (c), (d), and (e), and having a molecular weight of from about 1 million to about 10 million.

66. The product of claim 64 produced in 4 repetitions of steps (c), (d), and (e), and having a molecular weight of from about 10 million to about 50 million.

* * * * *

UNITED STATES PATENT AND TRADEMARK OFFICE
CERTIFICATE OF CORRECTION

PATENT NO. : 5,631,329
DATED : May 20, 1997
INVENTOR(S) : Yin et al.

Page 1 of 4

It is certified that error appears in the above-identified patent and that said Letters Patent is hereby corrected as shown below:

Column 1, line 41:
"in" should be --In--;

Column 2, line 23:
"polyaraidoamines" should be --polyamidoamines--;

Column 4, line 2:
"$R^a - \{(A^a) - (B^a)\}n^a G^a$" should be --$R^c - \{(A^c) - (B^c)\}n^c G^c$--

Column 5, line 1:
"$R^a$" should be --$R^c$--;

Column 6, line 49:
Delete "-";

Column 7, line 28:
"$-CH_2C(CH_2)_2-$" should be -- $-CH_2C(CH_3)_2-$ --;

Column 8, line 20:
"ba" should be --be--;

UNITED STATES PATENT AND TRADEMARK OFFICE
CERTIFICATE OF CORRECTION

PATENT NO. : 5,631,329
DATED : May 20, 1997
INVENTOR(S) : Yin et al.

It is certified that error appears in the above-identified patent and that said Letters Patent is hereby corrected as shown below:

Column 8, line 22:
"ba" should be --be--;

Column 8, line 26:
"polymarization" should be --polymerization--;

Column 8, line 40:
"-NCH$_2$CH$_2$" should be -- -NCH$_2$CH$_2$- --;
    |                      |
   H                    H Column 9, line 12:
"R$^a$ - {(A$^a$) — (B$^a$)}n $^a$ G$^a$" should be --R$^c$ - {(A$^c$)—(B$^c$)}n$^c$ G$^c$--;

Column 10, line 33:
"R$^a$-{(-CH$_2$CH$_2$NH-)(-CH$_2$CH$_2$N-)}n$^a$ G$^a$" should be
--R$^c$-{(-CH$_2$CH$_2$NH-) (-CH$_2$CH$_2$N-)}n$^c$ G$^c$--;

Column 13, line 46:
"mines" should be --amines--;

Column 13, line 55:
"mine" should be --amine--;

Column 14, line 8:
"mine" should be --amine--;

Column 14, line 25:
"mines" should be --amines--;

UNITED STATES PATENT AND TRADEMARK OFFICE
CERTIFICATE OF CORRECTION

PATENT NO. : 5,631,329
DATED : May 20, 1997
INVENTOR(S) : Yin et al.

Page 3 of 4

It is certified that error appears in the above-identified patent and that said Letters Patent is hereby corrected as shown below:

Column 14, line 27:
"mines" should be --amines-- (first occurrence);

Column 16, line 31:
"PHI" should be --PEI--;

Column 16, line 63:
"incrementaI" should be --incremental--;

Column 19, line 28:
"coversion" should be --conversion--;

Column 19, line 63:
"mixtrue" should be --mixture--;

Column 22, line 38:
"form" should be --from--;

Column 22, line 39:
"issolved" should be --dissolved--;

Column 23, line 36:
"sprial" should be --spiral--;

Column 24, line 44:
"cartiride" should be --cartridge--;

Column 25, line 59:
"temperqture" should be --temperature--;

Column 30, line 1:
"perforated" should be --performed--;

UNITED STATES PATENT AND TRADEMARK OFFICE
CERTIFICATE OF CORRECTION

PATENT NO. : 5,631,329
DATED : May 20, 1997
INVENTOR(S) : Yin et al.

Page 4 of 4

It is certified that error appears in the above-identified patent and that said Letters Patent is hereby corrected as shown below:

Column 31, claim 1, line 17:
"(1II)" should be --(III)--;

Column 31, claim 4, line 38:
"claim 3" should be --claim 2--;

Column 32, claim 10, line 12:
"claim 8" should be --claim 9--; and

Column 32, claim 11, line 14:
"claim 9" should be --claim 10--.

Signed and Sealed this

Third Day of February, 1998

BRUCE LEHMAN

Attest:

Attesting Officer

Commissioner of Patents and Trademarks